US007268224B2

(12) United States Patent
Vedeckis et al.

(10) Patent No.: US 7,268,224 B2
(45) Date of Patent: Sep. 11, 2007

(54) HUMAN GLUCOCORTICOID RECEPTOR 1A PROMOTER AND SPLICE VARIANTS

(75) Inventors: Wayne V. Vedeckis, Metairie, LA (US); Mary B. Breslin, Kenner, LA (US)

(73) Assignee: Board of Supervisors of Louisianna State University and Agricultural and Mechanical College, Baton Rouge, LA (US)

( * ) Notice: Subject to any disclaimer, the term of this patent is extended or adjusted under 35 U.S.C. 154(b) by 616 days.

(21) Appl. No.: 10/620,641

(22) Filed: Jul. 16, 2003

(65) Prior Publication Data

US 2004/0043023 A1 Mar. 4, 2004

Related U.S. Application Data

(62) Division of application No. 09/552,619, filed on Apr. 19, 2000, now Pat. No. 6,649,341.

(51) Int. Cl.
*A61K 38/16* (2006.01)
*C07H 21/04* (2006.01)

(52) U.S. Cl. .................. 536/23.5; 536/23.1; 435/69.1; 435/320.1; 435/252.3; 435/325

(58) Field of Classification Search ..................... None
See application file for complete search history.

(56) References Cited

OTHER PUBLICATIONS

The Journal Of Biological Chemistry, vol. 266, No. 11, Apr. 15, 1991, pp. 7182-7188.*
Amara, S.G. et al., "Alternative RNA Processing in Calcitonin Gene Expression Generates mRNAs Encoding Different Polypeptide Products," *Nature*, vol. 298, pp. 240-244 (1982).
Bradshaw, H.D., Jr. and W.V. Vedeckis, "Glucocorticoid Effects on Thymidine Incorporation into the DNA of S49 Lymphoma Cells," *J. Steroid Biochem.*, vol. 18, pp. 691-698 (1983).
Breslin, M.B. and W. V. Vedeckis, "The Glucocorticoid Receptor and c-*jun* Promoters Contain AP-1 Sites that Bind Different AP-1 Transcription Factors," *Endocrine*, vol. 5, pp. 15-22 (1996).
Breslin, M.B. and W. V. Vedeckis, "The Human Glucocorticoid Receptor Promoter Upstream Sequences Contain Binding Sites for the Ubiquitous Transcription Factor, Yin Yang 1," *J. Steroid Biochem. Molec. Biol.*, vol. 67, pp. 369-381 (1998).
Chen et al., "Association of the Glucocorticoid Receptor Alternatively-Spliced Transcript 1A with the Presence of the High Molecular Weight Membrane Glucocorticoid Receptor in Mouse Lymphoma Cells," *J. Cell. Biochem.*, vol. 74, pp. 430-446, (1999b).
Chen et al., "Multiple Glucocorticoid Receptor Transcripts in Membrane Glucocorticoid Receptor-Enriched S-49 Mouse Lymphoma Cells," *J. Cell. Biochem.*, vol. 74, pp. 418-429 (1999a).
DeAngelis, M.M. , "Assembly of a High-Resolution May of the Acadian Usher Syndrome Region and Localization of the Human Nuclear EF-Hand Acidic Gene," Biochim. Biophys. Acta, vol. 1407, pp. 84-91 (1998.
Denton, R.R. et al., "Differential Autoregulation of Glucocorticoid Receptor Expression in Human T- and B-Cell Lines," *Endocrinology*, vol. 133, pp. 248-256 (1993).

Distelhorst, C.W., "Basic and Clinical Studies of Glucocorticosteroid Receptors in Lymphoid Malignancies," pp. 494-515 in W. V. Vedeckis (ed.) *Hormones and Cancer* (1996).
Dong et al., "Regulation of Glucocorticoid Receptor Expression: Evidence for Transcriptional and Posttranslational Mechanisms," *Mol. Endocrinol.*, vol. 2, pp. 1256-1264 (1988).
Eisen, L. P. et al., "Positive Regulation of the Glucocorticoid Receptor in Human T-Cells Sensitive to the Cytolytic Effects of Glucocorticoids," *J. Biol. Chem.*, vol. 263, pp. 12044-12048 (1988).
Encio, I.J. and S.D. Detera-Wadleigh, "The Genomic Structure of the Human Glucocorticoid Receptor," *J. Biol. Chem.*, vol. 266, pp. 7182-7188 (1991).
Ferguson, A.T. et al., Demethylation of the Estrogen Receptor Gene in Estrogen Receptor-Negative Breast Cancer Cells Can Reactivate Estrogen Receptor Gene Expression, *Cancer Res.*, vol. 55, pp. 2279-2283 (1995).
Gasson, J.C. et al., "A New Determinant of Glucocorticoid Sensitivity in Lymphoid Cell Lines," *J. Cell. Biol.*, vol. 96, pp. 409-415 (1983.
Geley, S. et al., Resistance to Glucocorticoid-Induced Apoptosis in Human T-Cell Acute Lymphoblastic Leukemia CEM-C1 cells is Due to insufficient Glucocorticoid Receptor Expression. *Cancer Res.*, vol. 56, pp. 5033-5038 (1996).
Gomi, M. et al., "Glucocorticoid Effects on Myeloma Cells in Culture: Correlation of Growth Inhibition with Induction of Glucocorticoid Receptor Messenger RNA," *Cancer Res.*, vol. 50, pp. 1873-1878, (1990).
Grabowski, P.J., "Splicing Regulation in Neurons: Tinkering with Cell-Specific Control," *Cell*, vol. 92, pp. 709-712, (1998).
Günzburg, W. H. et al., "Regulated Gene Expression After Retroviral Vector-Mediated Delivery of Cancer-Relevant Therapeutic Genes," *Recent Results Cancer Res.*, vol. 144, pp. 116-126 (1998).
Harada, H. et al., "Structurally Similar but Functionally Distinct Factors, IRF-1 and IRF-2, Bind to the Same Regulatory Elements of IRFN and IFN-Inducible Genes," *Cell*, vol. 58, pp. 729-739 (1989).

(Continued)

*Primary Examiner*—Gary B. Nickol
*Assistant Examiner*—Nirmal S. Basi
(74) *Attorney, Agent, or Firm*—Bonnie J. Davis; John H. Runnels

(57) ABSTRACT

A new sequence, hGR 1Ap/e, has been isolated from human DNA upstream from the previously known 2.7 kbp human GR promoter region. This new sequence was found to contain a new promoter (the 1A GR promoter) and a new untranslated exon sequence (GR exon 1A) for the human glucocorticoid receptor protein (Hgr). Alternative splicing produces three different hGR 1A-containing transcripts, 1A1, 1A2, and 1A3. Exon 1A3-containing GR transcripts appear to be restricted to blood cell cancers and to the human brain. Glucocorticoid hormone treatment caused an up-regulation of exon 1A3-containing GR transcripts in T-lymphoblast cells, and a down-regulation of exon 1A3-containing transcripts in B-lymphoblast cells. Thus detection of exon 1A3-containing transcripts can be used for the diagnosis of patients with blood cell cancers, including T-cell acute lymphoblastic leukemia (ALL), and to identify patients that would benefit from glucocorticoid hormone treatment.

5 Claims, 15 Drawing Sheets

OTHER PUBLICATIONS

Hollenberg et al., "Primary Structure and Expression of a Functional Human Glucocorticoid Receptor cDNA," *Nature*, vol. 318, pp. 635-641 (1985).

Jonas, V. et al., Alternative RNA Processing Events in the Human Calcitonin/Calcitonin Gene-Related Peptide Gene Expression, *Proc. Natl. Acad. Sci. USA*, vol. 82, pp. 1994-1998 (1985).

Kalinyak, J.E.., "Tissue-specific Regulation of Glucocorticoid Receptor mRNA by Dexamethasone," *J. Biol. Chem.*, vol. 262, pp. 10441-10444 (1987).

Kroll, R.A. et al., "Outwitting the Blood-Brain Barrier for Therapeutic Purposes: Osmotic Opening and Other Means," *Neurosurgery*, vol. 42, pp. 1083-1099 (1998).

Lapidus, R.G. et al., "Methylation of Estrogen and Progesterone Receptor 5' CpG Islands Correlates with Lack of Estrogen and Progesterone Receptor Gene Expression in Breast Tumors," *Clin. Cancer Res.*, vol. 2, pp. 805-810 (1996).

Murayama, Y. et al., "Cell-Specific Expression of the Diphtheria Toxin A-Chain Coding Sequence Under the Control of the Upstream Region of the Human Alpha-Fetoprotein Gene," *J. Surg. Oncol.*, vol. 70, 145-149 (1999).

Nobukuni, Y. et al., "Characterization of the Human Glucocorticoid Promoter," *Biochemistry*, vol. 34, pp. 8207-8214 (1995).

Norman, M.R. and E. B. Thompson, "Characterization of a Glucocorticoid-Sensitive Human Lymphoid Cell Line," Cancer Res., vol. 37, pp. 3785-3791 (1977).

Okret, S. et al., "Down-Regulation of Glucocorticoid Receptor mRNA by Glucocorticoid Hormones and Recognition by the Receptor of a Specific Binding Sequence Within a Receptor cDNA Clone," *Proc. Natl. Acad. Sci. USA*, vol. 83, pp. 5899-5903 (1986).

Ottaviano, Y.L. et al., "Methylation of the Estrogen Receptor CpG Island Marks Loss of Estrogen Receptor Expression in Human Breast Cancer Cells," *Cancer Res.*, vol. 54, pp. 2552-2555 (1994).

Ramdas, J. et al., "Glucocorticoid-Induced Cell Death Requires Autoinduction of Glucocorticoid Receptor Expression in Human Leukemic T Cells," *Cancer Res.*, vol. 59, pp. 1378-1385 (1999).

Robertson, M.W., III, et al., "Use of a Tissue-Specific Promoter for Targeted Expression of the Herpes Simplex Thymidine Kinase Gene in Cervical Carcinoma Cells," *Cancer Gene Ther.*, vol. 5, pp. 331-336 (1998).

Roskrow, M.A. et al., "Recent Developments in Gene Therapy for Oncology and Hematology," *Crit. Rev. Oncol. Hematol.*, vol. 28, pp. 139-151 (1998).

Sharp, P.A., "Split Genes and RNA Splicing," *Cell*, vol. 77, pp. 805-815 (1994).

Sparmann, G. et al., "Conditional Expression of Human TNF-alpha: a System for Inducible Cytotoxicity," *Int. J. Cancer*, vol. 59, pp. 103-107 (1994).

Stevens, J. et al., "Characterization of Cytosolic and Nuclear Glucocorticoid-Binding Components in Human Leukemic Lymphocytes," *Cancer Res.*, vol. 39, pp. 4939-4948 (1979).

Strähle et al., "At Least Three Promoters Direct Expression of the Mouse Glucocorticoid Receptor Gene," *Proc. Natl. Acad. Sci. USA.*, vol. 89, pp. 6731-6735 (1992).

Tanaka, N. et al., "Recognition DNA Sequences of Interferon Regulatory Factor 1 (IRF-1) and IRF-2, Regulators of Cell Growth and the Interferon System," *Mol. Cell. Biol.*, vol. 13, pp. 4531-4538 (1993).

Thompson, E.B. et al., "Glucocorticoid Receptors in Human Leukemias and Related Diseases," *Klin. Wochenschr.*, vol. 63, pp. 689-698 (1985).

Vanderbilt, J.N. et al., "Intracellular Receptor Concentration Limits Glucocorticoid-Dependent Enhancer Activity," *Mol. Endocrinol.*, vol. 1, pp. 68-74 (1987).

Wei, P. and W. V. Vedeckis, "Regulation of the Glucocorticoid Receptor Gene by the AP-1 Transcription Factor," *Endocrine*, vol. 7, pp. 303-310 (1997).

Weis, L. and D. Reinberg, "Transcription by RNA Polymerase II: Initiator Directed Formation of Transcription Competent Complexes," *FASEB Journal*, vol. 6, pp. 3300-3309 (1992).

Zong, J. et al. "The Promoter and First, Untranslated Exon of the Human Glucocorticoid Receptor Gene are GC Rich but Lack Consensus Glucocorticoid Receptor Element Sites," *Mol. Cell. Biol.*, vol. 10, pp. 5580-5585 (1990).

* cited by examiner

```
-1075  ATTAGAGATT GTAAATTGGG CTCTGAGCTT CCTACCAACA AAAGCACAAA GGAAAATATG

-1015  ATCACTGGTA TTAAAAAAAA ACACCTATGG TTTCCAAAAG ATTAAAACAA ACCAGCAGTT

-955   TTATAGAAGC TAACACTAAA ATCTAAGGA ACTACGTTCT ATGGAGCCAC TTAATATGGA

-895   TAAACACTTT GACAATATTC TTTCAACAAC TACAGTAACA AGTTTCTTAG AGTCCATTTC

-835   TTTTTACATC CATAATGAAT TGTAAATCTT TTCTACTTCT TAAGTAAAAC ATCACCACTT

-775   AATTCTGGTA ACTTTTCCAT ATTAACTTTT TAGAACAATT GCAAACGTAC CATAAATGAT

-715   TGTTGTCACA GTGGTAACTA TTTGACCCTG ACTGTTATTT TGTATATAGC AGCTTTTAAA

-655   ATAAAAAGGC AACAAGTTTC TAGGCGTAAT TTCCACAGAT CTTTTATGTA AAACAATGAC

-595   ATCCTTTGCA ACTTCTGCCA TTTAATCTAT CTCAAGCAAG CTCTCTGGAA ACAAATCTAT

-535   TTGAAAGATT CTATTGTAAT TAGAAATCAG GGTAACTGAA TGCACTAGAT GAAAACCTTC

-475   TGACTGGGGC CAATGAAGTC AATAAAGTCA AAACTGCTGT GAATGCTCAA CTGTCTGCAG

-415   ATCAGATGTC TTGGGATGGA ATCCGTTCTC GAGGCCACCA TCATTAATAT CAATTTGGCC

-355   ATGTAATACA AGCCTCACTT GTTCCACTGT TACAAATGTG CTTAAAACTG AGCTCATTTA

-295   CAATCCAAAT ACATATGTAG GATGGTAACC AAGGCATCAC ACTAATTTAG GTATTATGTT
                                  ----------------------->
                                 FP1                          FP2
-235   TTAGGGGGAA CAAAAGG|TAT GTTAATATTT TATTCA|TC|TC CAAATTAACT ATAAATTGT|G
                                          FP3
-175   CATTCTTGCA TAGATCCTCC TTGGGAA|TGA GAAATTAGGA AAATCCA|GTT GTTAAAATGA
                                                                   FP4
-115   ATGCCTAAAA TCAAAATAAA ATTTGTTTTT CTGGCACCTG |CTTGATGACA CAGACTAATA|
                                                  ---------------------
                                                                    +1
-55    |ACCAATGA|CA AAATTCCCTT GAACCCAAGT TTTCATTTCC TCCTATTGTG TGGTCAGGTT
       ------>
```

Fig. 1-1

```
+6    ATGTAAGGGT TTGCTTTCAC CCCATTCAAA AGGTACCTCT TCCTCTTCTC TTGCTCCCTC
                                                                  ----------
                                                     FP5
+66   TCGCCCTCAT TCTTGTGCCT ATGCAGACAT TTGAGT|AGAG GCGAATCACT TTCACTTCTG|
      -------------->       ---------------------->
                                                                  FP6
+126  CTGGGGAAAT TGCAACACGC TTCTTTAAAT GGCAGAGAGA A|GGAGAAAAC TTAGATCTTC|
      ---------------------->
                        SD1 ↓
+186  |TGAT|ACCAAA TCACTGGACC TTAGAAGGTC AGAAATCTTT CAAGCCCTGC AGGACCGTAA
                                                    ---------------------->

+246  AATGCGCATG TGTCCAACGG AAGCACTGGG GCATGAGTGG GGAAGGAATA GAAACAGAAA

SD2 ↓
+306  GAGGGTAAGA GAAGAAAAAA GGGAAAGTGG TGAAGGCAGG GAGGAAAATT GCTTAGTGTG

+366  AATATGCACG CATTCATTTA GTTTTCAAAT CCTTGTTGAG CATGATAAAA TTCCCAGCAT

+426  CAGACCTCAC ATGTTGGTTT CCATTAGGAT CTGCCTGGGG AATATCTGC TGAATCAGTG
                                                    ---------------------->

+486  GCTCTGAGCT GAACTAGGAA ATTCACCATA ATTAGGAGAG TCACTGTATT TCTCTCCAAA

+546  AAAAAAAAAG TTATACCCGA GAGACAGGAT CTTCTGATCT GAAATTTTCT TCACTTCTGA

+606  AATTCTCTGG TTTGTGCTCA TCGTTGGTAG CTATTTGTTC ATCAAGAGTT GTGTAGCTGG

+666  CTTCTTCTGA AAAAAGGAAT CTGCGTCATA TCTAAGTCAG ATTTCATTCT GGTGCTCTCA

+726  GAGCAGTTAG CCCAGGAAAG GGGCCAGCTT CTGTGACGAC TGCTGCAGAG GCAGGTGCAG

+786  TTTGTGTGCC ACAGATATTA ACTTTGATAA GCACTTAATG AGTGCCTTCT CTGTGCGAGA

+846  ATGGGGAGGA ACAAAATGCA GCTCCTACCC TCCTCGGGCT TTAGTTGTAC CTTAATAACA

+906  GGAATTTTCA TCTGCCTGGC TCCTTTCCTC AAAGAACAAA GAAGACTTTG CTTCATTAAA
                                                                  ------------
                    SD3 ↓
+966  GTGTCTGAGA AGGAAG
      ---------------->
```

FIG. 1-2

```
-ATTAGAGAT----TGTAAATTGGGCTCTGAGCTTCCTA-CCAACAAAAGCACAAAGGAA
 : : ::::    ::: :: ::: :::: : ::: ::: ::: :::  :: :::   :
CACTGGAGAGAATCTGTTAACTGGCCTCTCATCTTTCTATCCAGCAAGCACAGAAAAACA

AATATGATCACTGGTATTAAAAAAAAACACCTATGGTTTCCAAAAGATTAAAACAAACCA
:: :::: :::: ::         ::   :::  :::: : :: :  :: ::   : ::
AAAATGACTACTGCTA---------AAAGTCTA--CTTTCTAGAA-ACCAACACGGAACA

GCAGTTTTATAGAAGCTAACACTAAAATCTAAAGGAACTACGTTCTATGGAGCCACTTAA
    :::::  :: : :::::  ::::  ::::::: :  :  ::::  ::::: :  :
----TTTTAG-GATGTTAACATTAAAGTCTAAAAAGTTCTGTTCAGCAGAGCCTCATGA

TATGGATAAACACTTTGACAATATTCTTTCAACAACTACAGTAACAAGTTTCTTAGAGTC
:::::  ::  ::::::: ::::: ::: ::: :::  : :: : :  ::::::::::::
TATGGGCAAGGACTTTGCCAATAATCTGTCAGCAAACATAGCATCTGCTTTCTTAAAGTC

CATTTCTTTT-TACATCCATAATGAATTGTAAATCTTTTCTACTTCTTAAGTAAAACATC
 :::: : : :::    : :::  :: :  : :  ::: : :::: ::: :: : :::
ACACTCTTCTGTTCTTCC----TAACTTGCAAGTAATCTCCATTTCTCAAGCAACA-ATC

ACCACTTAATTCTGGTAACTTTTC----CATATTAA-CTTTTTAGAACAATTGCAAACGT
 ::::::  :: ::: :::: :::    :::: ::: :: :: : :::: ::::: : ::
CCCACTTGATCCTGATAACCTTTTATTTCATAGTAAACTCTTGAAAACAGTTGCACATGT

ACCATAAA-TGATTGTTGTCACAGTGGTAACTATTTGACCCTGACTGTTATTTTGTATAT
:::: ::: ::::  ::: ::: ::: :: ::::::::: : : :  :::: ::::: :
ACCAGAAAATGATGCTTGACACCATGGAAATGATTTGACACAG-CAGTTACTTTGTCTCC

AGCAGCTTTTAAAATAAAAAGGCAACAAGTTTCTAGGCGTAATTTCCACAGATCTTTTAT
: ::: :                 :::  :::::::  : ::: :::  :    :::::
ACCAGTT-----------------ACACCTTTCTATAG--AGTTCCCATAGAGGCTTTAT

GTAAAACAATGACATCCTTTGC---------------AACT--TCTGCCATTTAATCTA
:::::  :: ::   :  :::                :::    :::  :::::::::::
GTAAAGCACTGGGGTGTTTTGTTTGTTTGTTTGTTTTAACAGCTCTACCATTTAATCAG

TCTCAAGCAAGCTCTCTGGAAACAAATCTATTTGAAAGATTCTATTGTAATTAGAAATCA
 ::  :: : :  :::    ::::: : ::::: :::: :::: :::::  :  ::: ::
CCTAGAGAATGATCT--AGAAACCAGTCTATCTGAAGGATTCTACTGAGTTTAGAATTTA

GGGTAACTGAATGCACTAGATGAAAACCTTCTGACTGGGGCCAATGAAGTCAATA-----
 : ::::: :   :    : :: : ::::::::: ::::  ::   :    ::::: :
GTATAACAGGAGAGAGTGGGTGAGACCCTTCTGA-TGGGCCC--TGAAGCCAAGAGCATT
```

Fig. 2-1

```
------------------AAGTCAAAA---------CTGCTGTGAATGCTCAACTGTCT
                  ::: ::: :         : ::: ::: ::: :::      :
GGCTCAGCTCTGAGTGCCCAAGCCAAGAGCATTGGCTCAGCTCTGAGTGCCCAAGCCATT

GCAGATCAGATGTCTTGGGATGGAATCCGTTCTCGAGGCCACCATCATTAATATCAATTT
::: : : ::: :::: ::::       :  ::::  ::::::   : :  ::    :::
GCACA-CTGCTGTGTTGGCATGG---CGTTTCTGCAGGCCATTGGTACTCTTACTGTTTT

GGCCATGTAATACAAGCCTCACTTGTTCCACTGTTACAAATGTGCTTAAAACTGAGCTCA
:::::::::::: ::     ::::::  :::  ::::: :::   :::::::::::: ::     ::
GGCCATGTAATTCATCGCTCACTA-TTCAACTGTGACAGGTGTGCTTAAAAC-GA---CA

TTTACAATCCAAATACATATGTAGGATGGTAACCAAGGCATCACACTAATTTAGGTATTA
 :   :   : ::   :  :::         ::::: :::: : :       ::::: :: :   :::
TAC-CTGTTCACAGCC-TAT-----ATGGTGACCAGGACCCTGAACTAACTTGGACCTTA

TGTTTTAGGGGGAACAAAAGGTATGTTAATATTTTATTCATCTCCAAATT---AACTATA
:::        ::     :  :::::::::     ::         :::::::::: :: :: : ::::::       :: : ::
TGT--CAGAAGCAACAAAAGACATACCAATATTTTCTTGATTTTCAAATTGGTAAGT-TA

AATTGTGCATTCTTGCATAGATCCTCCTTGGGAATGAGAAATTAGGAAAATCCAGTTGTT
::::::   :     ::::: :::::  :::  :   :           ::::  :::::     :::::    :
AATTGTCTACCCTTGCGTAGATTCTCTTCAGGC-----AAATGAGGAAGTGCCAGT---T

AAAATGAATGCCTAAAATCAAAATAAAATTTGTTTTTCTGGCACCTGCTTGATGACACAG
:::    :   ::     ::::::::::::: ::::    ::             ::::::::::::: ::::::            :
AAAGGTAGTGTGTAAAATCAAAACAAAAATTAAA---CTGGCACCTGCGTGATGAACAAA

ACTAATAACCAATGACAAAATTCCCTTGAACCCAAGTTTTCATTTCCTCCTAT-------
: :  :::::  :::::       : :::  :: :::    ::      :::::::::::::::  : :::
AATTATAATCAATGGTACAACTGTCT-GAAGTCA--TTTTCATTTCCTTCCATGAAGTGG

-------TGTGTGGTC
         ::::  ::  :
GCAGAGTTGTG-GGGC
```

Fig. 2-2

```
AGGTTATGTAAGGGTTTGCTTT-----------------CACCCCATTCAAAAGGTACCT
  : : :              ::                  : :::::  :   : ::  ::
TAACTCTCTTCTCTCCTCCCTTTCCCTCTCGGTCCTCCCCCCCCAACCCCCATGTCTCT

CTTCCTCT-TCTCTTGCTCCCTCTCGCCCTCATTCT-------TGT--------------
 ::   ::::  :::::   :::  :::::  : :::   :::             :::
CTCTCTCTCTCTCTCTCTCTCTCTCTCTCTCTCTCTCTGTTTTGGTTCCTTCTT

------------GCCTATGCAGACATTTGAGTAGAGGCGAATCACTTTCACTTCTGCTGG
             ::::      :::::        : ::::     : ::::::  :::::::::::::
GCTCTTTTTAGGGCCTGCACAGACCCACGGGTAGCCACTGATCACTCTCACTTCTGCTGA

GGAAATTGCAACACGCTTCTTTAAATGGCAGAGAGAAGGAGAAAACTTAGATCTTCTGAT
::::::    ::  ::  :::::::  :::::::   ::    :::  :::::::::   ::::  :::::::
GGAAATGACAGCATGCTTCTCTAAATGGTGGAACGAAAGAGAAAAC--AGATGTTCTGAT

ACCAAATCACTGGACCTTAGAAGGTCAGAAATCTT-TCAAGCCCTGCAGGACCGTAAAAT
:::::::       :::  ::  ::  :::  :: : :::  ::: :  ::  :  :::::::  ::  :::
ACCAAATGGTCAGACTTTGGAGGGTTAGCAGTATTCTCAGGACCAGTAGGACC-TAGAAT

GCGCATGTGTCCAACGGAAGCACTGGGGCATGAGTGGGGAAGGAATAGAAACAGAAAGAG
        ::  :::   :   :  :::::::::::  : :  ::::::    :  :     ::::     ::
AT--CTGAGTCTGAAG--AGCACTGGGGAGTCACTGGGGGGTGGGT-----CAGA---AG

GGTAAGAGAAGAAAAAAGGGAAAGTGGTGAAGGCAGGGAGGAAAATTGCTTAGTGTGAAT
:::::  :::::::::  ::::         :::             :::  :::    :    ::   ::::  : :
ACTAAGACAAGAAAAA-GGGA----GGT-------GGGCGGA---TGTCTGTGTGTTA-T

ATGCACGCATTCATTTAGTTTTCAAATCCTTGTTGAGCATGATAAAATTCCCAGCATCAG
::: :             : :   ::::   : : :   ::::::::   ::  ::        : : :
CTGCTC-------------TGCTGATCCCTCTCGTGCATGATGCAACACCTGACTTTAA

ACCTCACATGTTGGTTTCCATTAGGATCTGCCTGGGGGAATATCTGCTGAATCAGTGGCT
::::           :::::::  :::  ::  ::::   ::  :::::  :::::::::::::::::::::  ::
CCCTCTTGCTATGGTTTCTATTTGGGTCTGACTTGGGGACTATCTGCTGAATCAGTATCT
```

Fig. 3-1

```
CTGAGCTGAACTAGGAAATTCACCATAATTAGGAGAGTCACTGTATT--------TCTCT
::::::  ::::  :  ::::::::::::    :   ::   ::::::::::::::      :::::
CTGAGCAGAACCAAGAAATTCACCCCCAA-AGAGGAGTCACTGTATTAGTCAGGGTCTCT

CCAAAAAAAAAAAAGTTATACCCGAGAGACAGGATCTTCTGATCTGAAATTTTCTTCACT
         ::  ::::::::  ::::  :::   ::::  :::  ::::  :::::::::::   :::  :
G-------AACAAAGTTAGACCCAAGAAACAGAATCCTCTGGTCTGAAATGGTCT-CTTG

TCTGAAATTCTCTGGTTTGTGCTCATCGTT-----------GGTAGCTATTTGTTCATCA
:  ::::::::::::::  :::::  :  ::   :                      :::::      ::  ::  :::
TGTGAAATTCTCTGCTTTGTACGCAAAGGAAAGAACATGCCGGTAGGAGCCTGCTCGTCA

A--GAGTTGTGTAGCTGGCTTCTTCTGAAAAAAGGAATCTGCGTCATATCTAAGTCAGAT
:    :::  ::::  :  ::  ::::::::::    :::::::  :    ::::::::::  :::   :::   :::::
AACGAGGTGTGAATCTAGCTTCTTCTAGAAAAAGCAGCCTGCGTCACATCGAAGCCAGAT

TTCATTCTGGTGCTCTCAGAGCAGTTAGCCCAGGAAAGGGGCCAGCTTCTGTGACGACTG
::  ::::    ::::::  :::::  :::::  :  ::    ::::  :   :::::  :::::   ::::
TTGGTTCTT-TGCTCTGAGAGCGGTTAGGCTAGTGGAGGG-CAGGCTTCCGTGACAACTG

CTGCAGAGGCAGGTGCAGTTTGTGTGCCACAGATATTAACTTTGATAAGCACTTAATGAG
:  :::   :  ::::::::::  ::   ::  :::::::::::  ::::   ::::::     :      :::::
GTACAGGGACAGGTGCAGTGTGGGTCCCACAGATATGAACTCTGATAAATCGTGCATGAG

TGCCTTCTCTGTGCGAGAATGGGGAGGAACAAAATGCAGCTCCTACCCTCCTCGGGCTTT
::  :::::    :   ::::::::   ::   ::     :      :::::::     ::::::::::::    :::    :
---CTACTCTGCGTAAGAATGGAGAAGAGAGCAGCCCAGCTCCCACCCTCCTGGGGTTCC

AGTTGTACCTTAATAACAGGAATTTTCATCTGCCTGGCTCCTTTCCTCAAAGAACAAAGA
:  :  :  :  ::                 :::::::   :::  :    ::   :  :  :::   :
CATCGCAGCCTGAT-----------CATCTGCA-GCCTTC--TCAGCCAGGAAGATGTT

--AGACTTTGCTTCATTAAAGTGTCTGAGAAGGAAG
   :::      :::::::  :::  :::::::::::  :  ::::::
TCAGATCCTGCTTCGTTAGAGTGTCTG-GGAGGAAG
```

Fig. 3-2

HUMAN GLUCOCORTICOID RECEPTOR 1A PROMOTER AND SPLICE VARIANTS

This is a divisional of application Ser. No. 09/552,619, filed Apr. 19, 2000, now issued as U.S. Pat. No. 6,649,341.

The development of this invention was partially funded by the Government under grant no. DK47211 from the National Institutes of Health. The Government has certain rights in this invention.

This invention pertains to the location of a human glucocorticoid receptor gene promoter region and to three splice variants of the human glucocorticoid receptor gene; and the use of the promoter region and of the splice variants to improve the diagnosis and treatment of leukemia.

The use of naturally occurring substances, such as hormones, to treat cancer has certain advantages. Although side effects can occur, the effects are usually less severe than those caused by cytotoxic chemotherapy. Unfortunately most cancers are not effectively controlled by hormonal therapy, but exceptions include certain hormonally-dependent breast cancers that can be treated with the anti-estrogen tamoxifen, and acute promyelocytic leukemia that is responsive to all-trans retinoic acid. Additionally, some lymphoid malignancies can be effectively treated with glucocorticoid steroid hormones, hormones that control a variety of metabolic and developmental processes. See R. R. Denton et al., "Differential Autoregulation of Glucocorticoid Receptor Expression in Human T- and B-Cell Lines," *Endocrinology*, vol. 133, pp. 248-256 (1993). Certain types of B- and T-cell acute lymphoblastic leukemia ("ALL") are particularly sensitive to glucocorticoid hormonal therapy. Glucocorticoids affect lymphoid malignancies due to the induction of programmed cell death, or apoptosis, of immature lymphocytes. See C. W. Distelhorst, "Basic and Clinical Studies of Glucocorticosteroid Receptors in Lymphoid Malignancies," pp. 494-515 in W. V. Vedeckis (ed.) *Hormones and Cancer* (1996).

The cytolytic effect of glucocorticoids is mediated by the glucocorticoid receptor (GR). Upon entering the cell, glucocorticoids bind to the soluble intracellular receptor protein GR, causing an alteration in GR structure. This alteration in structure converts the unactivated receptor to the activated form that both binds to specific DNA sequences and facilitates transcription of glucocorticoid-responsive genes. The transcribed glucocorticoid-induced mRNA messages are then transported into the cytoplasm and translated into specific proteins. The changes in concentration and types of the intracellular proteins modulate a variety of intracellular processes. GR concentration has been shown to correlate with sensitivity to steroid treatment in vitro. See J. N. Vanderbilt et al., "Intracellular Receptor Concentration Limits Glucocorticoid-Dependent Enhancer Activity," *Mol. Endocrinol.*, vol. 1, pp. 68-74 (1987). Additionally, an in vivo study of large numbers of patients with ALL found that a low GR level in lymphoblasts isolated at the initial diagnosis was significantly correlated with a poor response to therapy, shorter duration of remission, and a poor overall prognosis. Distelhorst (1996).

Studies have shown that chronic glucocorticoid treatment of cells that do not respond by apoptosis resulted in a decrease in expression (or down-regulation) of the GR gene, as evidenced by decreased levels of GR mRNA and protein. See S. Okret et al., "Down-Regulation of Glucocorticoid Receptor mRNA by Glucocorticoid Hormones and Recognition by the Receptor of a Specific Binding Sequence Within a Receptor cDNA Clone," *Proc. Natl. Acad. Sci. USA*, vol. 83, pp. 5899-5903 (1986); and Dong et al., "Regulation of Glucocorticoid Receptor Expression: Evidence for Transcriptional and Posttranslational Mechanisms," *Mol. Endocrinol.*, vol. 2, pp. 1256-1264 (1988). By contrast, in cells that undergo apoptosis upon glucocorticoid treatment, such as immature thymocytes, T-lymphocytes, and leukemic T-lymphoblasts, glucocorticoid treatment caused a dramatic increase in the levels of GR mRNA and protein levels, indicating an increase in expression (or up-regulation) of the GR gene. Denton et al. (1993). The molecular mechanisms that control down-regulation and up-regulation of the GR gene are not understood.

Studies on the structure of the human GR gene have shown that the mature GR mRNA is coded by nine separate exons in the genomic DNA. See I. J. Encio and S. D. Detera-Wadleigh, "The Genomic Structure of the Human Glucocorticoid Receptor," *J. Biol. Chem.*, Vol. 266, pp. 7182-7188 (1991). Exon 1 is an untranslated exon; i.e., it is transcribed into mRNA but does not code for amino acids in the GR protein. Exon 2 contains the ATG methionine initiator for protein translation. Thus any exon 1 sequences that are spliced onto exon 2 will have no effect on the amino acid sequence of the GR, because the protein coding sequence begins in exon 2, and also because there is an in-frame stop codon located three codons upstream of the initiator ATG in exon 2. Exon 9 codes a long 3' untranslated region in the GR mRNA that contains two potential polyadenylation addition sites. The two major, mature GR mRNA species are about 7 kilobases and 5 kilobases long, depending upon which polyadenylation site is used. Additionally, an alternative splicing event in exon 9 gives rise to two GR protein forms, GR alpha and GR beta. GR alpha is the major, functional species found in all cell types. The function, if any, of GR beta is not clear.

The GR promoter region, which controls GR gene expression and mRNA synthesis, has been investigated in both the human and mouse. The human GR promoter was found to be ~2.7 kilobase pairs (kbp). See J. Zong et al. "The Promoter and First, Untranslated Exon of the Human Glucocorticoid Receptor Gene are GC Rich but Lack Consensus Glucocorticoid Receptor Element Sites," *Mol. Cell. Biol.*, vol. 10, pp. 5580-5585 (1990) and Y. Nobukuni et al., "Characterization of the Human Glucocorticoid Promoter," *Biochemistry*, vol. 34, pp. 8207-8214 (1995). This GR promoter is GC-rich and lacks a TATA box and CAAT box, common characteristics of "housekeeping" genes that are constitutively expressed in most cell types.

The GR protein is found in virtually all cells in the human body. Regulatory elements that control GR gene expression have been characterized in the 2.7 kbp human GR promoter region, just upstream from the untranslated exon 1. See Nobukuni et al. (1995); M. B. Breslin and W. V. Vedeckis, "The Glucocorticoid Receptor and c-jun Promoters Contain AP-1 Sites that Bind Different AP-1 Transcription Factors," *Endocrine*, vol. 5, pp. 15-22 (1996), P. Wei and W. V. Vedeckis, "Regulation of the Glucocorticoid Receptor Gene by the AP-1 Transcription Factor," *Endocrine*, vol. 7, pp. 303-310 (1997), and M. B. Breslin and W. V. Vedeckis, "The Human Glucocorticoid Receptor Promoter Upstream Sequences Contain Binding Sites for the Ubiquitous Transcription Factor, Yin Yang 1," *J. Steroid Biochem. Molec. Biol.*, vol. 67, pp. 369-381 (1998). Eleven regions in the first 800 bp of the promoter have been identified that bind protein. Of these eleven, three regions bind the transcription factor Sp1, two regions bind Sp1 and another protein, and one region binds predominantly the transcription factor AP-2, as well as some Sp1. The binding of Sp1 to GC-rich regions is typical of housekeeping, constitutive promoters.

See Nobukuni et al. (1995). A single untranslated exon in the 2.7 kbp human GR promoter gene fragment has also been identified. See Zong et al., (1990) and I. J. Encio and Detera-Wadleigh (1991). The start sites for transcription that were identified in the human GR promoter region were somewhat variable, which is another characteristic of a promoter for a housekeeping gene.

The mouse GR promoter and gene structure have also been characterized. See Strähle et al., "At Least Three Promoters Direct Expression of the Mouse Glucocorticoid Receptor Gene," *Proc. Natl. Acad. Sci. USA.*, vol. 89, pp. 6731-6735 (1992). Similar to human, the mouse GR transcript derives from 9 exons, and the ATG methionine initiator is in exon 2. However, two exon 1 sequences that derive from the mouse promoter analogous to the human 2.7 kpb sequence have been identified. The one nearest to exon 2 has been designated exon 1C, and is homologous to the human GR exon 1 sequence. See Nobukuni et al., 1995. Further upstream is untranslated exon 1B, found about 1 kbp upstream from the exon 1C sequence. An additional untranslated exon (1A) was found on some GR transcripts. The genomic sequence that coded for exon 1A was located far upstream (~32 kbp) from the mouse GR promoter sequence that gives rise to the exon 1B and 1C G transcripts. Thus mouse GR mRNA transcripts derive from three separate promoters, which give rise to three GR transcripts that differ in the untranslated exon 1 region (1A, 1B, or 1C). Significantly, exon 1B- and 1C-containing mouse GR transcripts were detected in all tissues and cells studied, namely brain, liver, fibroblast, and T-lymphoma cell lines. However, exon 1A-containing transcripts were only found in two T-cell lymphoma cell lines, leading to the conclusion that the mouse 1A promoter was cell-specific for T lymphocytes. There is substantial sequence homology between the 2.7 kbp human GR promoter and that of mouse exons 1B and 1C.

Other alternative transcripts for the mouse GR gene have recently been described. See Chen et al., "Multiple Glucocorticoid Receptor Transcripts in Membrane Glucocorticoid Receptor-Enriched S-49 Mouse Lymphoma Cells," *J. Cell. Biochem.*, vol. 74, pp. 418-429 (1999a). Both of the previously-described exons 1A and 1B (but not exon 1C) were found in GR transcripts in the mouse S49 lymphoma cell line. Two new untranslated exon 1-containing mouse GR transcripts were also discovered (exons 1D and 1E). Exon 1D genome sequences are located ~300 bp upstream of the exon 1B region. Exon 1E sequences overlap with exon 1C sequences, but contain sequences not found in exon 1C. The exon 1A-containing transcript was present in high amounts in cells that were enriched for a membrane-associated form of the GR, compared to cells that had low levels of membrane GR, e.g., S49 cells selected for low membrane GR levels and mouse AtT-20 pituitary tumor cell line.

The mouse GR promoter and exon 1A sequences have been characterized. See Chen et al., "Association of the Glucocorticoid Receptor Alternatively-Spliced Transcript 1A with the Presence of the High Molecular Weight Membrane Glucocorticoid Receptor in Mouse Lymphoma Cells," *J. Cell. Biochem.*, vol. 74, pp. 430-446 (1999b). Using a variety of techniques, a new exon (termed 1A), based on the nomenclature of Strähle et al. (1992), was identified. Exon 1A is 1013 bp in length. Transcripts that contain exon 1A were suggested to result in the synthesis of a larger, membrane-associated GR, whose presence correlates with apoptosis in a mouse lymphoma cell line. Only one exon 1A-containing mouse GR transcript was identified. A putative promoter region of the 1A-containing transcripts was postulated. This was based upon the fact that the sequences (2140 bp) upstream of the identified start site of exon 1A were not found to be transcribed into RNA in the cell. Computer analysis indicated possible transcription factor binding sites that might be consistent with this being a promoter region. Transfection of the full-length exon 1A-containing GR cDNA into mouse AtT-20 pituitary cells and human HL-60 myeloid leukemia cells, followed by hormone treatment, resulted in cell death. These studies suggested that the exon 1A-containing mouse GR mRNA was a necessary factor for hormone-induced cell death, since the steroid hormone alone does not normally kill these two cell lines.

A mechanism used to generate different protein products is alternative RNA splicing of transcripts that are controlled by the same promoter. Alternative splicing of a precursor to different mature mRNA transcripts is a complicated process. A variety of small nuclear RNA's and proteins form complexes with the pre-mRNA, and splicing involves specific sequences at the splice donor site, splice acceptor site, and the branch point. P. A. Sharp, "Split Genes and RNA Splicing," *Cell*, vol. 77, pp. 805-815 (1994). In some cases, as for the calcitonin/calcitonin-related peptide system, alternative splicing of protein-coding exons gives rise to different protein products with different biological functions. S. G. Amara et al., "Alternative RNA Processing in Calcitonin Gene Expression Generates mRNAs Encoding Different Polypeptide Products," *Nature*, vol. 298, pp. 240-244 (1982). V. Jonas et al., Alternative RNA Processing Events in the Human Calcitonin/Calcitonin Gene-Related Peptide Gene Expression," *Proc. Natl. Acad. Sci. USA*, vol. 82, pp. 1994-1998 (1985). Differential mRNA splicing can occur in a cell type- and developmental stage-specific manner, and can be regulated by both positively-acting (stimulatory) and negatively-acting (repressive) cell specific protein factors. P. J. Grabowski, "Splicing Regulation in Neurons: Tinkering with Cell-Specific Control," *Cell*, vol. 92, pp. 709-712 (1998).

In a clinical setting, there is a need for a method for determining the GR status of a patient to help design an effective therapeutic strategy. A patient with lymphoid malignancies such as ALL frequently develops glucocorticoid resistance, which leads to a relapse even though initial glucocorticoid treatment resulted in the killing of leukemic cells and a remission. See Distelhorst (1996). Thus, although relapsed ALL patients are non-responsive to glucocorticoid treatment, they are still at risk for developing the side-effects of corticosteroid therapy, including hypertension, hyperglycemia, and immunosuppression. In addition, the continued glucocorticoid treatment of a glucocorticoid-resistant patient may preclude the use of more aggressive chemotherapy due to the patient's poor condition caused by the side-effects of corticosteroid therapy. Thus, there exists a need to be able to identify glucocorticoid-resistant patients, in both newly diagnosed and relapsed ALL patients.

We have discovered a new sequence, hGR 1Ap/e, isolated from human DNA upstream from the previously known 2.7 kbp human GR promoter region. This new sequence was found to contain a new promoter (the human 1A G promoter) and a new untranslated exon sequence (human GR exon 1A) that occurs in the mRNA that also contains the sequence that codes for the human glucocorticoid receptor protein (hGR). The hGR 1Ap/e sequence is approximately 25 kilobase pairs upstream of the hGR coding sequence. Alternative splicing produces three different hGR 1A-containing transcripts, 1A1, 1A2, and 1A3. GR transcripts containing exons 1A1, 1A2, 1B (in the proximal promoter region), and 1C (in the proximal promoter region) are expressed at various levels in many cancer cells and in human brain. Exon 1A3-containing GR transcripts appear to be restricted to blood cell cancers and to human brain. Glucocorticoid hormone treatment caused an up-regulation of exon 1A3-containing GR transcripts in T-lymphoblast cells, and a down-regulation of exon 1A3-containing transcripts in B-lymphoblast cells. These alterations correlate with the known responses of the two cells to glucocorticoid hormone treatment, i.e., B-lymphoblast cells are known to be resistant to glucocorticoid hormone treatment and T-lymphoblast cells are known to be sensitive. Thus the presence of exon 1A3-containing transcripts can be used to detect cancerous blood cells that would be sensitive to glucocorticoid hormone treatment. Additionally, an interferon regulatory factor element (IRF-E) that binds IRF-2 was found in the exon 1A sequence. This regulatory factor appears to contribute significantly to basal transcription rate of 1A G transcripts. The intraexonic location of this sequence was surprising. A glucocorticoid response element (GRE) was also found intraexonically in the exon 1A sequence. The presence of these two regulatory factors indicates that both interferon and glucocorticoid hormone could be used to increase the level of exon 1A3-containing transcripts in the cells. There are ~1075 base pairs of hGR 1A promoter sequence, based upon the absence of these sequences in mRNA. There are ~981 bp of exon 1A sequence. The portions of the hGR 1Ap/e sequence that can function as a eukaryotic promoter or as intraexonic regions that influence promoter activity were identified based on reporter gene assays. The detection of exon 1A3-containing transcripts can be used for the diagnosis of patients with T-cell acute lymphoblastic leukemia (ALL) and other glucocorticoid-responsive cancers, and to identify patients who would benefit from glucocorticoid hormone treatment.

BRIEF DESCRIPTION OF THE DRAWINGS

FIGS. 1-1 through 1-2 documents the DNA sequence of the hGR 1Ap/e region, SEQ ID NO: 1. The putative transcription start (CAP) site is denoted as base 1. The boxed series of bases indicate regions protected using DNAse I footprinting. The primer sequences are indicated by dashed arrows under the sequence. The vertical arrows illustrate splice donor sites. The italicized sequence indicates the portion of the sequence of which the complimentary strand is a portion of GenBank Accession # AA917693 (with two mismatches).

FIGS. 2-1 through 2-2 illustrates the alignment of the hGR 1Ap/e promoter sequence, SEQ ID NO: 2, the top sequence, with the mouse 1A promoter sequence, SEQ ID NO: 3, (Chen et al., 1999b) using the ALIGN program.

FIGS. 3-1 through 3-2 illustrates the alignment of the hGR 1Ap/e exon sequence, SEQ ID NO: 4, the top sequence, with the mouse 1A exon sequence, SEQ ID NO: 5, (Chen et al., 1999b) using the ALIGN program.

Figure 4:
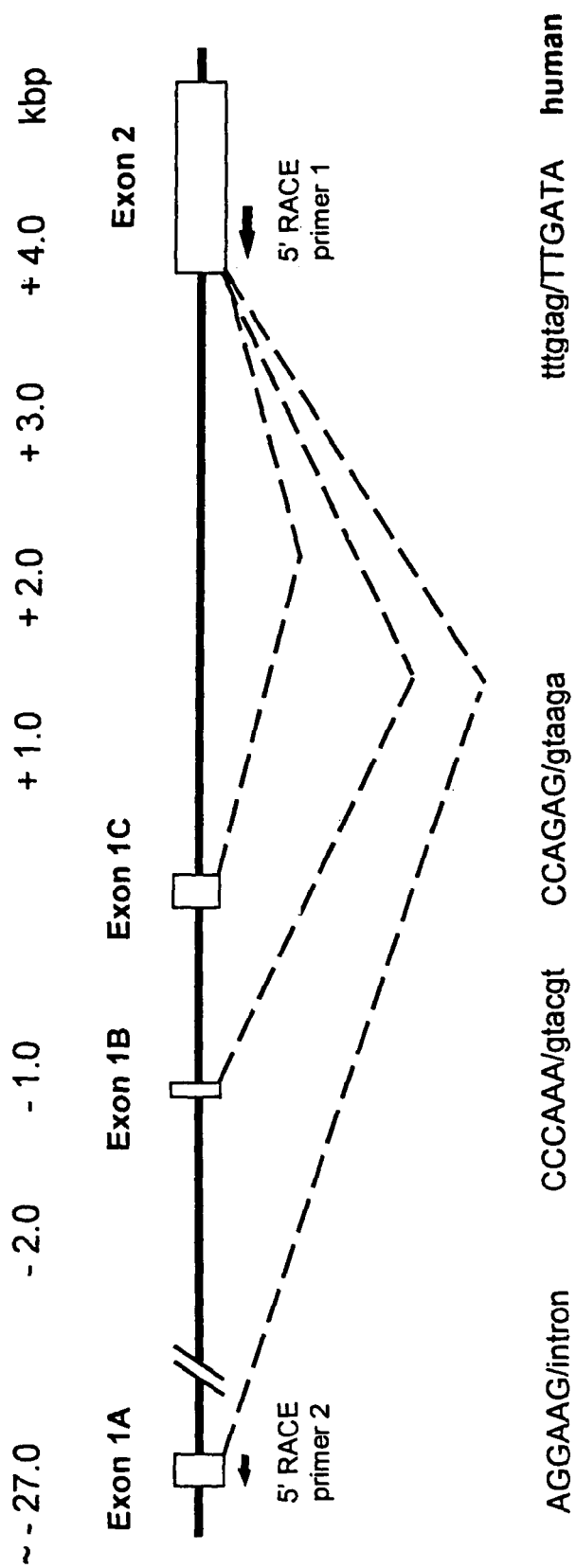
FIG. 4 illustrates a schematic diagram of the genomic structure of the human GR (hGR) promoters and the GR gene up to exon 2.

The hGR 1Ap/e sequence (SEQ ID NO: 1, FIG. 1) has not been previously disclosed. The hGR 1Ap/e sequence shows a 60.6% identity to the mouse GR 1A promoter and exon in the putative promoter region (FIG. 2), and 61.6% in the exon 1A region (FIG. 3), as analyzed using the ALIGN program (http://vega.igh.cnrs.fr/bin/align-guess.cgi). It is unknown whether the mouse and human 1A sequences represent homologous genetic loci.

We have identified, sequenced, and named a new human GR untranslated exon-coding sequence exon 1A, which gives rise to three different untranslated 5' splicing variants—exon 1A1, exon 1A2, and exon 1A3. We named the new untranslated exon "exon 1A" based upon the mouse exon 1 nomenclature, and on the similarity between the previously known human untranslated exon 1 sequence and location, and the untranslated mouse exons 1B and 1C. We have shown that exon 1A3 is selectively expressed in cancer cell lines derived from white blood cells, including a human T-cell acute lymphoblastic leukemia (ALL) cell line, CEM-C7. Thus the detection of exon 1A3 transcripts in patients can be used to diagnose leukemia and to detect early relapse in leukemia patients. Primers have been developed for the detection of exon 1A3 sequences in patients using the reverse transcriptase-polymerase chain reaction (RT-PCR). We have also cloned, sequenced, and characterized a new human GR promoter (GR promoter 1A).

The novel hGR 1A p/e is involved in the up-regulation of GR gene expression in T-lymphoblasts. Either the 1A promoter and/or exon sequence can be used to diagnose the hormone responsiveness of patients at initial presentation and at relapse. By assaying glucocorticoid-stimulated GR gene expression in peripheral blood cells, one may determine quickly whether a patient is expected to be responsive or resistant to glucocorticoid hormone treatment. Blood cells can be isolated, exposed to glucocorticoid, and the expression of the exon 1A3 sequence assayed. Patients may be monitored during their treatment, remission, or relapse to determine whether they are still responsive or have converted to a glucocorticoid-resistant state. This technique also permits early detection of glucocorticoid resistance, which allows a more informed, rational strategy for secondary chemotherapy. For example, when a glucocorticoid-resistant patient is identified, a clinician can design alternative strategies such as dose escalation or the use of alternative drug combinations that might otherwise be contraindicated by concurrent glucocorticoid treatment.

EXAMPLE 1

Sequencing of the hGR 1Ap/e Region

A MOLT-4 (T-cell acute lymphoblastic leukemia) Marathon-ready double strand cDNA library (CLONTECH Laboratories, Palo Alto, Calif.) was used in a 5' RACE (rapid amplification of complementary DNA ends) reaction. All DNA primers that were used in this and in subsequent examples are listed in Table 1.

NO: 9) (CLONTECH). G3PDH is a constitutively expressed gene, and the detection of its expression confirmed that the 5'-RACE reaction was working successfully. The RACE reaction contained 0.5 ng MOLT-4 cDNA library, 10 µM each of the 5' and 3' primers, 0.2 mM dNTPs (CLONTECH), 1× Advantage Taq PCR buffer (CLONTECH), and 1× Advantage Taq DNA polymerase (CLONTECH) in a 50 µl reaction. The PCR reaction was performed in a GeneAmp PCR System 9600 Thermocycler (Perkin-Elmer Corpora-

TABLE I

DNA Primers

| Primer Name | Sequence | Source |
|---|---|---|
| 5' AP-1 | 5' CCATCCTAATACGACTCACTATAGGGC 3' (SEQ ID NO: 6) | CLONTECH |
| exon 2 primer #1 | 5' GGGTTTTATAGAAGTCCATCACATCTCC 3' (SEQ ID NO: 7) | Hollenberg et al. (1985)* |
| exon 2 primer #2 | 5' CGACAGCCAGTGAGGGTGAAGACG 3' (SEQ ID NO: 8) | Hollenberg et al. (1985)* |
| G3PDH | 5' GACCACAGTCCATGACATCACT 3' (SEQ ID NO: 9) | CLONTECH |
| -2101 to -1783 upstream primer | 5' TCCGACACTGTACCCTACCAAG 3' (SEQ ID NO: 10) | Zong et al. (1990) |
| -2101 to -1783 downstream primer | 5' TCCGACGATGCCGGGACCGAGCC 3' (SEQ ID NO: 11) | Zong et al. (1990) |
| antisense +955/+978 | 5' CCTTCTCAGACACTTTAATGAAGC 3' (SEQ ID NO: 12) | Inventor Designed |
| exon 1A3 | 5' GCTTCATTAAAGTGTCTGAGAAGG 3' (SEQ ID NO: 13) | Inventor Designed |
| exon 1A1 | 5' GTGAATATCAACTTCTAAGGTCCAGTG 3' (SEQ ID NO: 14) | Inventor Designed |
| exon 1A2 | 5' GTGAATATCAACTCTTTCTGTTTC 3' (SEQ ID NO: 15) | Inventor Designed |
| exon 1B | 5' GCAACTTCTCTCCCAGTGGCG 3' (SEQ ID NO: 16) | Zong et al. (1990) |
| exon 1C | 5' CTTAAATAGGGCTCTCCCCC 3' (SEQ ID NO: 17) | Zong et al. (1990) |
| exon 1A (-372/-353) | 5' GGTAACCAAGGCATCACACT 3' (SEQ ID NO: 18) | Inventor Designed |
| exon 1A (-174/-149) | 5' GATGACACAGACTAATAACCAATG 3' (SEQ ID NO: 19) | Inventor Designed |
| exon 1A (+56/+77) | 5' TTGCTCCCTCTCGCCCTCATTC 3' (SEQ ID NO: 20) | Inventor Designed |
| exon 1A (+126/+146) | 5' CTGGGGAAATTGCAACACGC 3' (SEQ ID NO: 21) | Inventor Designed |
| exon 1A (+222/+241) | 5' CTTTCAAGCCCTGCAGGACC 3' (SEQ ID NO: 22) | Inventor Designed |
| exon 1A (+456/+475) | 5' CTGCCTGGGGAATATCTGC 3' (SEQ ID NO: 23) | Inventor Designed |
| exon 1A (+84/+103, antisense) | 5' CTACTCAAATGTCTGCATAG 3' (SEQ ID NO: 24) | Inventor Designed |
| FP5 deletion oligo | 5' GCAATTTCCCCAGCAGTGATTCGCCTCTACTC 3' (SEQ ID NO: 25) | Inventor Designed |
| FP6 deletion oligo | 5' CAGTGATTTGGTATCTCTAAGTTTTCTCCTTCTC 3' (SEQ ID NO: 26) | Inventor Designed |
| FP5 (+) oligo | 5' GTAGAGGCGAATCACTTTCACTTCTGCTGGG 3' (SEQ ID NO: 27) | Inventor Designed |
| FP5 (-) oligo | 5' CCCAGCAGAAGTGAAAGTGATTCGCCTCTAC 3' (SEQ ID NO: 28) | Inventor Designed |
| FP6 (+) oligo | 5' GAGAAGGAGAAAACTTAGATCTTCTGATACCAA 3' (SEQ ID NO: 29) | Inventor Designed |
| FP6 (-) oligo | 5' TTGGTATCAGAAGATCTAAGTTTTCTCCTTCTC 3' (SEQ ID NO: 30) | Inventor Designed |

*Hollenberg et al., "Primary Structure and Expression of a Functional Human Glucocorticoid Receptor cDNA," Nature, vol. 318, pp. 635-641 (1985).

5'RACE was performed using a 5' AP-1 primer (SEQ ID NO: 6) (CLONTECH) and two separate 3' primers to exon 2 of the human GR gene, exon 2 primer #1 (SEQ ID NO: 7) and exon 2 primer #2 (SEQ ID NO: 8). See Hollenberg et al. (1985). A control 5' RACE reaction was performed with the 5' AP-1 primer (SEQ ID NO: 6) and a 3' glyceraldehyde 3-phosphate dehydrogenase (G3PDH) gene primer (SEQ ID tion, Norwalk, Conn.) with an initial denaturation at 94° C. for 1 minute; 5 cycles of 94° C. for 10 seconds, 72° C. for 3 minutes; 5 cycles of 94° C. for 10 seconds, 70° C. for 3 minutes; followed by 25 cycles of 94° C. for 10 seconds, 68° C. for 3 minutes. The PCR products were analyzed on a 1.2% agarose/1×TBE gel containing 0.1 µg/ml ethidium bromide. The band of interest was excised from the gel and purified using the GENECLEAN III kit (BIO 101, Inc., Vista, Calif.). The gel-purified DNA was ligated into the pCR2.1 TA cloning vector (Invitrogen, Carlsbad, Calif.). Clones were sequenced using the exon 2 human GR gene primers (#1 and #2) (SEQ ID NOS. 6 and 7) using a Thermo Sequenase Kit (USB Corporation, Cleveland, Ohio). Numerous individual clones were sequenced using primers #1 and #2 from exon 2. Seventeen clones were identified as containing human GR exon sequences that were distinct from exon 2. These were identified as upstream sequences that were not in exon 2. Five non-exon 2 sequences corresponded to the known human 1C exon, 11 contained a new sequence which mapped to the human equivalent of the mouse 1B promoter and exon, and 1 sequence was not found in the 2.7 kbp of the published human GR promoter. See Zong et al. (1990). This last sequence had 54 base pairs (bp), and was designated as the 3' end of the putative human hGR 1A exon, since it was distinct from the exon 2 sequences and was not in the known 2.7 kbp hGR promoter and exon sequences.

Screening for alternative human GR promoter and exon regions was performed using a total human genomic BAC library, Release III (Research Genetics, Inc., Huntsville, Ala.). The BAC library contains approximately 221,000 independent clones in a 96-well microtiter plate format. The human BAC library was screened by polymerase chain reaction (PCR). The PCR primers amplified the −2101 to −1783 bp hGR promoter region from the published sequence containing promoter and exon 1B and 1C sequences, (upstream primer, SEQ ID NO: 10, and downstream primer, SEQ ID NO: 11). See Zong et al. (1990). All oligonucleotide primers were purchased from Sigma-Genosys (The Woodlands, Tex.). The PCR reactions were performed using 1 µg BAC DNA, 1 mM $MgCl_2$, 5 mM dNTP's (New England Biolabs, Inc., Beverly, Mass.), 20 pmole each of an upstream (5') and downstream (3') primer, 1×PCR buffer (Perkin-Elmer), and 1 unit AmpliTaq DNA polymerase (Perkin-Elmer) in a 25 µl reaction. The PCR reaction was performed in a GeneAmp PCR System 9600 Thermocycler (Perkin-Elmer) with a denaturation step of 95° C. for 5 minutes; 35 cycles of 94° C. for 1 minute, 60° C. for 1 minute; 72° C. for 1 minute; and a final extension of 72° C. for 5 minutes. A positive control, 20 ng HeLa genomic DNA isolated from tissue culture cells, was run in parallel with the PCR reactions. See F. M. Ausubel et al., eds., in *Current Protocols in Molecular Biology*, John Wiley & Sons, Inc., New York, N.Y. (1994). The PCR products were analyzed on a 2% agarose/1×TBE gel. BAC DNA was isolated from a 10 ml overnight culture using the alkaline lysis method. See J. Sambrook et al., "Molecular Cloning: A Laboratory Manual," $2^{nd}$ Edition, Cold Spring Harbor Laboratory Press, Cold Spring Harbor, N.Y. (1989). Three BAC clones were identified containing sequences −2101 to −1783 of the human GR promoter, which had previously been identified by Nobukuni et al. (1996). Direct sequencing of the BAC DNA was performed using the Thermo Sequenase Kit.

Southern blot analysis was performed, as described in Ausubel et al. (1994), using a nick-translated probe to determine if the 54 bp exon 1A region (positions +928 to +981 in SEQ ID NO: 1) was contained in the isolated BAC clones. Two of the BAC clones, I13 and G6, contained the 54 bp exon 1A (+928/+981) region, indicating that this sequence was on the same piece of human genomic DNA (chromosome 5) that contained the human GR 1B and 1C promoters. Pulsed Field Gel Electrophoresis, as described in M. M. DeAngelis et al., "Assembly of a High-Resolution Map of the Acadian Usher Syndrome Region and Localization of the Human Nuclear EF-Hand Acidic Gene," Biochim. Biophys. Acta, vol. 1407, pp. 84-91 (1998), indicated that this new sequence was located ~25 kilobases upstream (5') of the GR 1B promoter. (Data not shown.) A schematic diagram of the genomic structure of the GR promoters, untranslated exons, and the gene up to exon 2 is shown in FIG. 4.

A new antisense primer (positions +955 to +978), SEQ ID NO: 12, for a portion of the 54 bp putative human GR 1A exon was designed and used for cycle sequencing (as described above) of one of the BACs to extend the 1A exon sequence farther upstream into the putative human GR 1A promoter. To date, 2056 bp have been sequenced, the last 54 bp of which are the new human GR 1A exon (+928/+981) sequence originally isolated from the RACE cDNA library. This sequence (SEQ ID NO: 1) is shown in FIG. 1. This sequence, named "hGR 1Ap/e," includes transcribed regions corresponding to human GR 1A exons and untranscribed regions that include a promoter. This entire sequence was not found in the GenBank or EMBL DNA sequence databases (see below). It is about 61% homologous to the mouse GR 1A promoter and exon (as reported by Chen et al., 1999), as analyzed using the ALIGN program (http://vega.igh.cnrs.fr/bin/align-guess.cgi). The alignment is shown in FIGS. 2 and 3.

While the entire hGR 1Ap/e sequence was not found in the genome databases, a portion of the non-coding strand was found in a clone obtained from a human kidney cDNA library (GenBank Accession # AA917693). There are 435 nucleotides of sequence reported for AA917693. The sequence from 255 to 435 in AA917693 corresponds to the complementary strand from +794 to +974 in SEQ ID NO: 1. There are two discrepancies in the kidney cDNA sequence and SEQ ID NO: 1 (the "A" at position +872 in SEQ ID NO: 1 is a "G" instead of a "T" on the complementary strand at position 357 in AA917693, and the "C" in position +873 in SEQ ID NO: 1 is a "T" instead of a "G" on the complementary strand at position 356 in AA917693). We have confirmed by repeated sequencing that the sequence of SEQ ID NO: 1 is correct. There are at least two possible explanations for these discrepancies. First, the reported sequence for AA917693 may contain an error. Second, there could be two naturally occurring polymorphisms at these positions in the human genome. With these two nucleotide differences, SEQ ID NO: 1 was 98% identical (179/181 nucleotides) to AA917693. However, the sequence completely diverged from the genomic sequence in SEQ ID NO: 1 from positions −1075 to +793. Sequence −1075 to +793 was not found in AA917693. Furthermore, positions 1 to 254 in AA917693 were not found in SEQ ID NO: 1. Also, when a part of the downstream (3') genomic DNA from SEQ ID NO: 1 was sequenced, it did not match positions 1-254 in AA917693. The relevance of these observations is unknown. No physiological function has been reported for this cDNA isolated from human kidney cells.

EXAMPLE 2

Alternative Splicing of the Human GR 1A Promoter/Exon Sequence

Using the reverse transcriptase-polymerase chain reaction (RT-PCR; using the CLONTECH "RT-for-PCR" kit) and DNA cloning (using the "pCR II TA TOPO" Cloning kit, Invitrogen), three alternative splice sites for exon 1A were found. Total RNA was collected from 24 hour ethanol or 1 µM dexamethasone-treated cells using TriReagent (Molecular Research Center, Cincinnati, Ohio), according to the manufacturer's directions. One microgram of total RNA was reverse-transcribed using random hexamer primers (CLONTECH's RT-for-PCR kit), and the resulting cDNA was diluted to 100 μl final volume. PCR reactions were performed with two different upstream primers (+56/+77 and +126/+146, see below) that were common to all three transcripts, and with the exon 2 primer listed below. Three transcripts of differing length were observed (data not shown). PCR was performed in a 25 μl reaction volume with an initial denaturation step of 94° C. for 2 minutes, followed by 94° C. for 30 sec, 68° C. for 30 sec, and 72° C. for 30 sec. With the exon 1A1/exon 2 and exon 1A2/exon 2 primer sets, the annealing temperature was 64° C. for 30 sec. Quantum-RNA™ 18S internal control primers (1:9 primer:competimer ratio) (Ambion, Inc., Austin, Tex.) were included in each reaction to normalize the data. Primer sets used for RT-PCR included exon 1A3 (SEQ ID NO: 13), exon 1A1 (SEQ ID NO: 14), exon 1A2 (SEQ ID NO: 15), exon 1B (SEQ ID NO: 16), exon 1C (SEQ ID NO: 17), and the 3' primer for all of the primer sets was hGR exon 2 primer #2 (SEQ ID NO: 8). The first three primers were designed for use, while the latter three were found in the literature. See Zong et al. (1990). The exon 1A1 and 1A2 primers actually contain a portion of exon 2. It was necessary to span the splice junction to obtain primers selective for these two transcripts, such that each primer hybridized only to its cognate cDNA and did not hybridize to the other two exon 1A splice variants. Primers to determine the 5' end of the exon 1A transcripts included exon 1A (−372/−353) (SEQ ID NO: 18), exon 1A (−174/−149) (SEQ ID NO: 19), exon 1A (+56/+77) (SEQ ID NO: 20), exon 1A (+126/+146) (SEQ ID NO: 21), exon 1A (+222/+241) (SEQ ID NO: 22), and exon 1A (+456/+475) (SEQ ID NO: 23). All of these primers were designed for this use. The downstream primer used was the hGR exon 2 primer #2 (SEQ ID NO: 8). All three forms of exon 1A were found to be spliced to the same splice acceptor site in exon 2, as determined by direct DNA sequencing. All three variants of exon 1A were non-coding (i.e., were not translated into protein), as shown by the in-frame stop codon located three codons upstream of the initiator ATG (methionine) sequence in exon 2.

Figure 5:
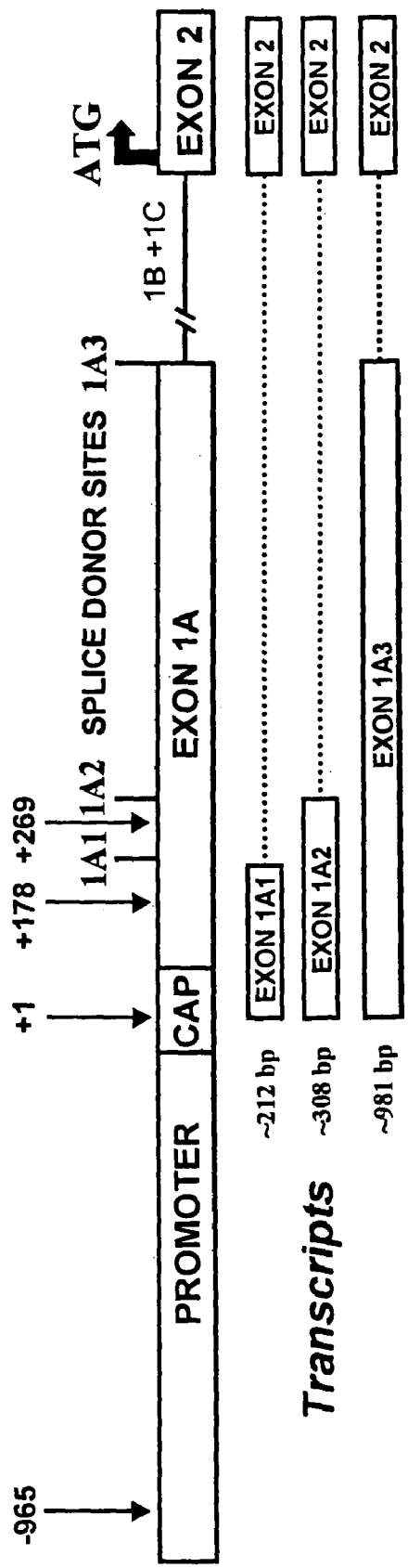
FIG. 5 illustrates the relationships of the three exon 1A transcripts to the hGR 1A promoter and the GR gene up to exon 2.

Exon 1A 1 extended from the transcription initiation site (currently undetermined, but estimated to be at the +1 position indicated in SEQ ID NO: 1, as described in Example 3) until the G residue at position +212 of SEQ ID NO: 1. Exon 1A2 extended from the initiation site of transcription until the G residue at position +308 of SEQ ID NO: 1. Exon 1A3 extended from the transcription initiation site until the G residue at position +981 of SEQ ID NO: 1. The three splice sites were determined by direct sequencing of individual clones obtained from 5' RACE of the mRNA obtained from the cells, as described above. FIG. 5 illustrates the relationships of the three exon 1A transcripts that we have discovered.

EXAMPLE 3

Identification of Possible Transcription Initiation Site

The position of the transcription initiation (CAP) site that gives rise to the 5' terminus of the mRNA was identified as follows. When upstream primers from positions −372/−353 or −174/−149 were used for RT-PCR with a downstream primer from exon 2, 3, 4, 5, 6, 7, 8 or 9, no product was obtained. This lack of product indicated that the region between positions −372 and −149 is not transcribed. When an upstream primer from positions +56/+77 was used with the same downstream primers, products were obtained, indicating that this sequence is transcribed into an exon. Thus, the most probable transcription initiation (CAP) site is between positions −149 and +56.

The +1 start site of transcription was determined using primer extension analysis (Ausubel et al., 1994) and RT-PCR. The primer exon 1A (+84/+103, antisense) (SEQ ID NO: 24) used for primer extension analysis was γ$^{32}$P ATP-labeled using T$_4$ polynucleotide kinase (New England BioLabs). The labeled primer was purified using the Qiaquick Nucleotide Removal Kit (Qiagen, Inc., Valencia, Calif.). An aliquot of 10 picomoles of the γ-$^{32}$P ATP labeled exon 1A primer was mixed with 20 μg of total RNA from CEM-C7 cells or IM-9 cells. The primer was annealed to the RNA by heating at 90° C. for 1 minute, followed by 70° C. for 10 minutes, and then immediately placed on ice. The extension mixture included 1× first strand synthesis buffer (0.25 M Tris-HCl (pH 8.3), 375 mM KCl, 15 mM MgCl$_2$), 5 mM DTT, and 0.5 mM dNTPs. The mixture was incubated at 42° C. for 2 minutes prior to the addition of 200 U Superscript RT (Gibco BRL, Gaithersburg, Md.). The primer was extended at 42° C. for 50 min, and the reaction was stopped by heating at 70° C. for 10 min. The RNA template was digested with 2 μl RNase One cocktail (20 U) (Promega Corp., Madison, Wis.) for 30 minutes at 37° C. The resulting products were extracted with phenol/chloroform, then precipitated with ethanol, and resolved on a 7 M urea 6% denaturing PAGE. The longest labeled fragment that gave a strong stop was mapped to position +1 in SEQ ID NO: 1 (FIG. 1). This position was designated the most likely candidate for the 5'-0 CAP (initiation site) for exon 1A transcript sequences. Because the individual exon 1A1, 1A2, and 1A3 sequences could not be completely determined by the splice sites to their 5' ends, it could not be conclusively shown that each of the three transcripts initiated at the same CAP site. Although more than one promoter in the 2056 bp of SEQ ID NO: 1 is a possibility, promoter analysis argues against this conclusion (see Examples 8 and 9 below). Therefore, each of the three exon 1A transcripts (1A1, 1A2, and 1A3) most likely initiate at the same CAP site, but splice alternatively at their 3' ends. Using the indicated +1 position as the CAP site and assuming that all three exon 1A transcripts initiate at this site, the lengths of the three splice variants were determined: exons 1A1, 212 nucleotides; exon 1A2, 308 nucleotides; and exon 1A3, 981 nucleotides (FIG. 5).

EXAMPLE 4

Expression of Human GR Exon 1 Transcripts in Various Cancer Cell Lines

Figure 6:
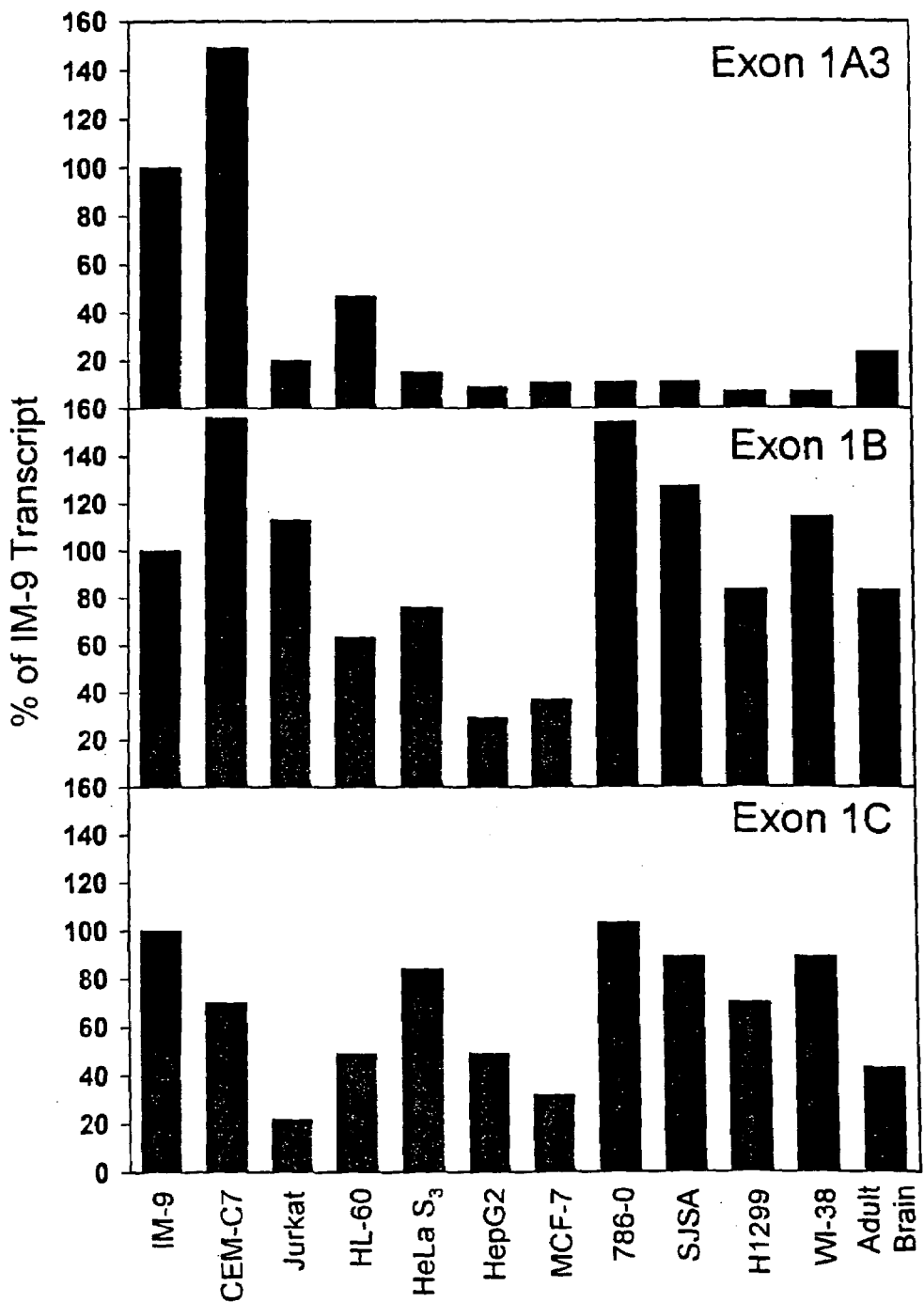
FIG. 6 illustrates the expression of hGR exon 1A3, 1B, and 1C transcripts in various cell lines and adult brain tissue.

To assay for transcription of the different human GR exons 1A1, 1A2, 1A3, 1B, and 1C in different cell lines, mRNA from the cell lines listed in Table 2 and from human brain tissue was isolated. Then RT-PCR was conducted using primers specific for each of the three human GR exons, as described above in Example 2. The upstream, exon-specific primers are listed in Table 1 (exon 1A1 (SEQ ID NO: 14), exon 1A2 (SEQ ID NO: 15), exon 1A3 (SEQ ID NO: 13), exon 1B (SEQ ID NO: 16), exon 1C (SEQ ID NO: 17)). The downstream primer for all reactions was exon 2 primer #2 (SEQ ID NO: 8). Transcripts containing GR exons 1B and 1C were found to be ubiquitously expressed in all cell lines, as shown in FIG. 6. This result is consistent with the literature reporting that the GR protein and its mRNA are found in all cell types. See J. E. Kalinyak et al., "Tissue-specific Regulation of Glucocorticoid Receptor mRNA by Dexamethasone," *J. Biol. Chem.*, vol. 262, pp. 10441-10444 (1987). This result is additional evidence that the 1B and 1C promoters control constitutively expressed "housekeeping" genes. L. Weis and D. Reinberg, "Transcription by RNA Polymerase II: Initiator Directed Formation of Transcription Competent Complexes," *FASEB Journal*, vol. 6, pp. 3300-3309 (1992).

TABLE 2

| Human Cell Line | Type of Cell |
| --- | --- |
| IM-9 | B-Cell Leukemia |
| CEM-C7 | T-Cell Leukemia |
| Jurkat | T-Cell Leukemia |
| HL-60 | Acute Myelogenous Leukemia (AML-M2) |
| HeLa $S_3$ | Cervical Cancer |
| HepG2 | Hepatocarcinoma |
| MCF-7 | Breast Cancer |
| 786-0 | Kidney Cancer |
| SJSA | Osteosarcoma. |
| H1299 | Lung Cancer |
| WI-38 | Normal Fibroblast |
| Adult Brain | Brain Tissue |

Figure 7:
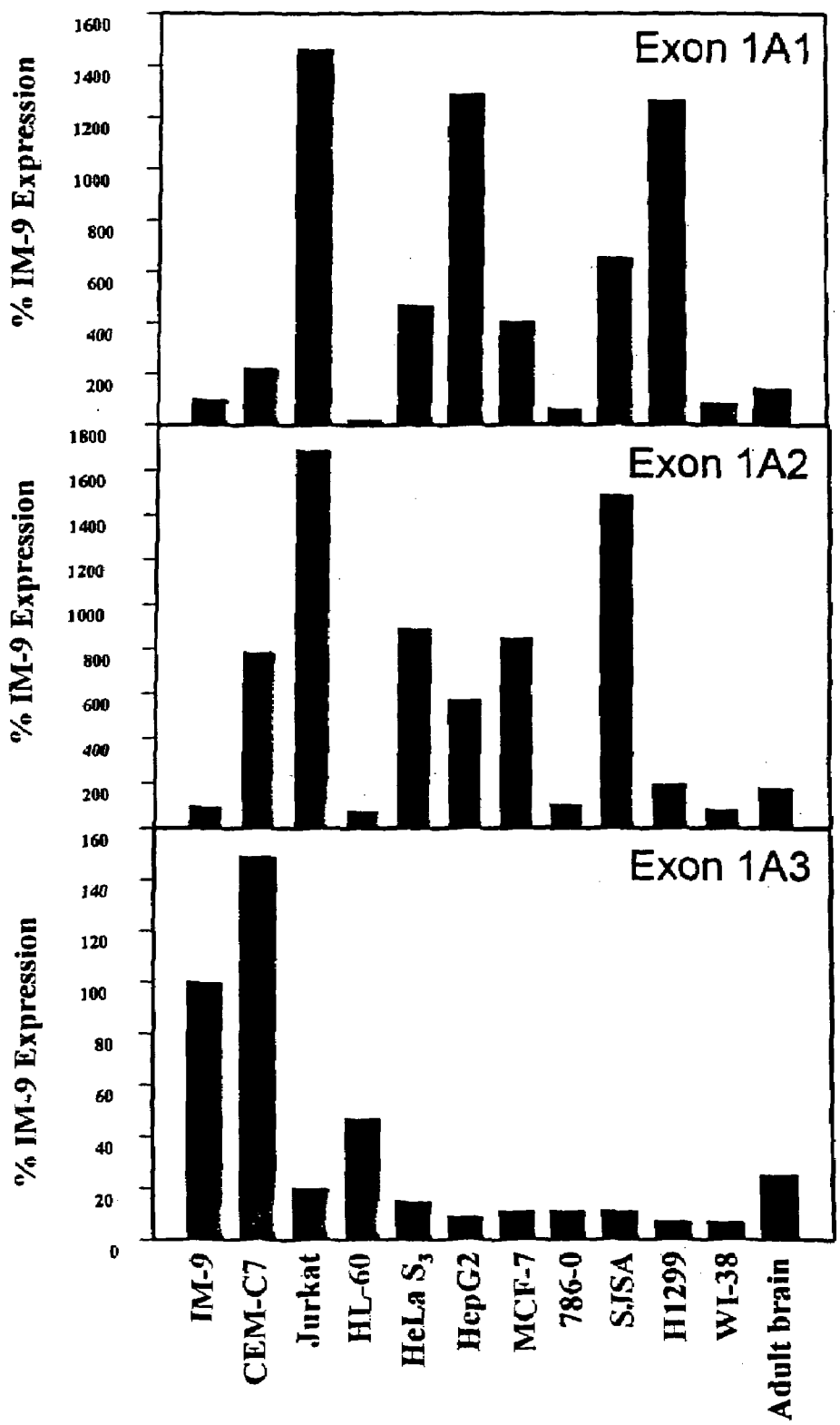
FIG. 7 illustrates the expression of hGR exon 1A1, 1A2, and 1A3 transcripts in various cell lines and adult brain tissue.

The above cells and tissues showed varying levels of transcription from the GR exon 1B and 1C promoters (FIG. 6). Also, varying levels of the exons 1A1- and 1A2-containing GR transcripts were detected in the different cells (FIG. 7). However, exon 1A3-containing transcripts were found in significant amounts only in leukemia cells, with a lower level occurring in human brain tissue. None of the solid tumor cell lines (carcinomas and sarcoma) had substantial amounts of detectable GR 1A3-containing transcripts. In contrast, all leukemia cells tested had GR 1A3-containing transcripts, including T-cell acute lymphoblastic leukemia cells that are known to be killed by glucocorticoids, e.g., the CEM-C7 cells. In contrast, Jurkat cells are known not to be killed by glucocorticoids. This result indicates that the presence of significant amounts of GR 1A3 transcripts in peripheral blood leukocytes may have broad applicability for the detection of a wide variety of leukemias in patients, or for monitoring relapse following treatment.

EXAMPLE 5

Glucocorticoid Up-Regulation of the Human GR 1A3 Exon Transcript

Glucocorticoid hormone treatment is known to up-regulate the levels of both GR mRNA and GR protein in immature T-lymphocytes and in some T-lymphoblasts that undergo apoptosis following hormone treatment. See Denton et al., (1993); and L. P. Eisen et al., "Positive Regulation of the Glucocorticoid Receptor in Human T-Cells Sensitive to the Cytolytic Effects of Glucocorticoids," *J. Biol. Chem.*, vol. 263, pp. 12044-12048 (1988). The human CEM-C7 acute lymphoblastic leukemia (ALL) cell line has served as a model system for glucocorticoid-sensitive human T-cell ALL. See M. R. Norman and E. B. Thompson, "Characterization of a Glucocorticoid-Sensitive Human Lymphoid Cell Line," Cancer Res., vol. 37, pp. 3785-3791 (1977). CEM-C7 cells were treated with 1 µM dexamethasone (a glucocorticoid analogue) for various periods of time, from 6 hr to 48 hr. RNA was then extracted, and northern blots were prepared and probed with the GR-1A-exon-specific probes (exon 1A1, exon 1A2, and exon 1A3; Table 1). A dramatic increase of GR 1A3 exon-containing transcripts was seen in the human CEM-C7 cells after 6 and 24 hours of glucocorticoid treatment (data not shown). Up-regulation of exon 1A1 and exon 1A2 transcripts was also observed (data not shown). Longer-term hormonal treatments were not possible in this experiment because the cells underwent apoptosis and were dying 48 hours after dexamethasone treatment.

Figure 8:
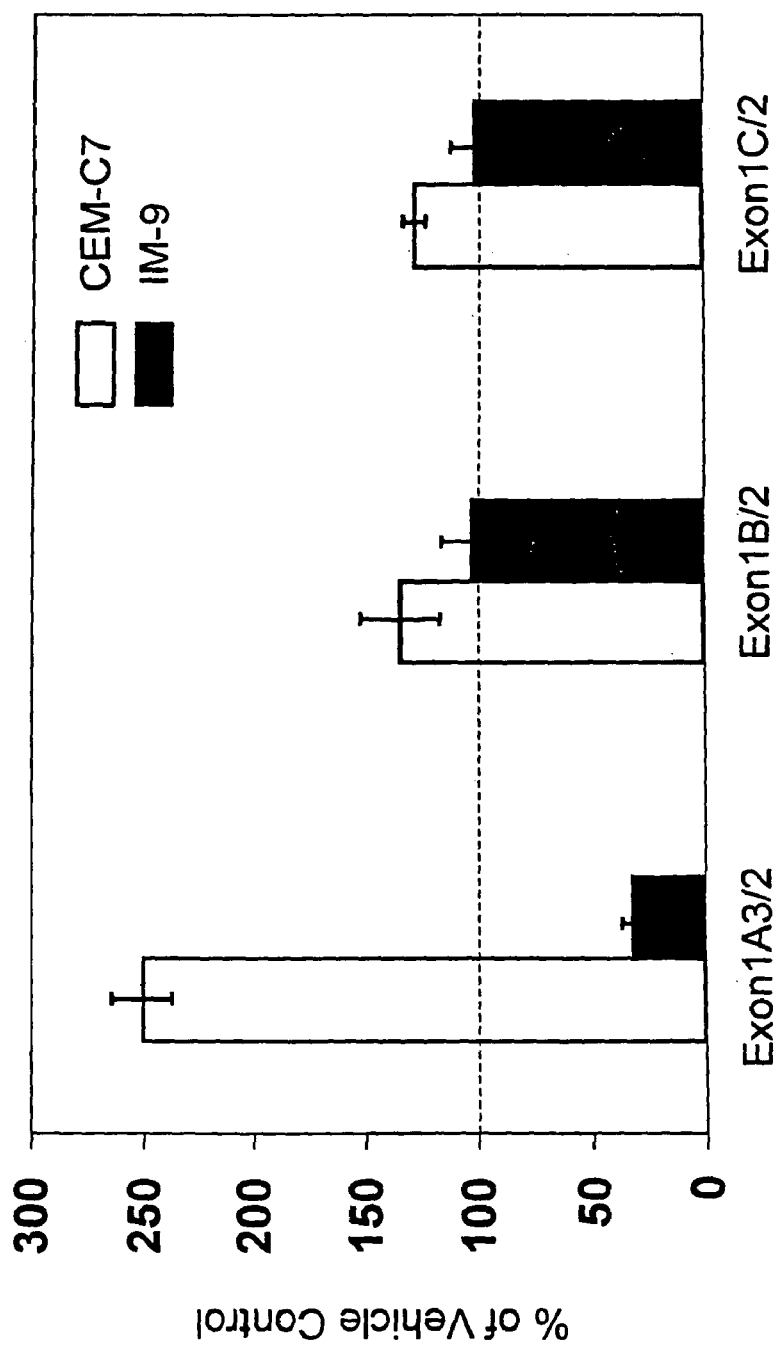
FIG. 8 illustrates the effects of glucocorticoid treatment on expression of GR exon 1 transcripts in two leukemia cell lines.

The above experiments were repeated in both CEM-C7 and IM-9 cells using RT-PCR as described above, and the effects of hormone-treatment on expression of exon 1B- and exon 1C-containing transcripts were evaluated. Exon 1B- and 1C-containing transcripts were only slightly elevated by 1 µM dexamethasone-treatment in CEM-C7 cells, while the level of these transcripts was unaffected in IM-9 cells (FIG. 8). In CEM-C7 cells, in which glucocorticoid hormone causes an up-regulation of total GR mRNA levels, a 2.5-fold increase in exon 1A3-containing transcripts was seen following treatment with dexamethasone. However, in IM-9 cells, in which glucocorticoid hormone causes a down-regulation of total GR mRNA levels, the level of 1A3-containing transcripts was reduced following treatment with dexamethasone. The results with the 1A3-containing transcripts were similar to results previously obtained for total GR mRNA levels in these two cell types. See Denton et al., 1993. Thus, the regulation of GR mRNA by a glucocorticoid analog, both upward in CEM-C7 cells and downward in IM-9 cells, was parallel to that for GR 1A3-containing transcripts. Although 1A1- and 1A2-transcripts were up-regulated in CEM-C7 cells, determination of down-regulation after hormonal treatment in IM-9 cells was not measurable because of the already very low level 1A3-transcripts in these cells before hormone treatment. (See FIG. 7). These results indicate that the differential regulation of GR mRNA levels in CEM-C7 cells (up-regulation) and IM-9 cells (down-regulation) was largely due to the effect of hormone on exon 1A3-containing GR transcripts.

EXAMPLE 6

The GR 1A3 Transcript is Normally Expressed in Tissues Containing Immature T-Cells To demonstrate that GR 1A3 expression is present in normal immature T-cells and is not merely an artifact seen in T-cell lines that have been in tissue culture for a very long time, normal human thymus RNA, which should contain some immature T-cells, was purchased from CLONTECH to assay for GR exon 1A3 expression. CEM-C7 cells, a T-cell leukemia cell line, were used as a positive control. Using RT-PCR with the exon 1A3 (SEQ ID NO: 13) and exon 2 primer #1 (SEQ ID NO: 7) sequences (Table 1), GR 1A3-containing transcripts were identified in human thymus RNA, thus indicating that this is a normally occurring species of GR mRNA. (Data not shown). CEM-C7 cells showed strong expression of GR 1A3-containing transcripts, as demonstrated previously. While transcripts with GR exons 1A1 and 1A2 were detected in the CEM-C7 ALL cancer cell line, they were not detected in normal human thymus. Without wishing to be bound by this theory, we believe that one explanation for this difference may be that the normal GR 1A-containing transcript is 1A3, and that the 1A1 and 1A2 variants may only be expressed in cancer cell lines that have been cultured in vitro.

EXAMPLE 7

Exon 1A3 Transcripts Found in a Leukemia Patient

RNA from normal human peripheral blood leukocytes (PBL), and RNA from the bone marrow of a patient newly diagnosed with T-cell acute lymphoblastic leukemia (ALL) were tested for the presence of GR 1A3-containing transcripts using the same RNA extraction procedure described in the previous examples, and the same RT-PCR protocol described in Example 6. No GR 1A-containing transcripts were detected in normal human PBLs, while a strong signal was obtained from the bone marrow from the T-cell ALL patient. (Data not shown). Furthermore, the exon containing 1A3, but not exon 1A1 or exon 1A2, was identified in the bone marrow from the T-cell ALL patient. (Data not shown). This is further evidence that the exon 1A3-containing transcript is the relevant species in vivo. These results indicated that a rapid RT-PCR assay is sufficiently selective to identify patients that have T-cell ALL. While PBL's (rather than bone marrow) from an ALL patient have not yet been tested, it is expected that the early onset of ALL could be detected by assaying peripheral lymphoblast cells for increased levels of the 1A3-GR transcript. Additionally, because RT-PCR analysis of normal PBL cell RNA did not detect any 1A3 transcript, this assay should not give false positives in normal individuals who are disease-free. Commercial kits are currently available to isolate PBL RNA and perform RT-PCR, enabling one of ordinary skill in the art, given the present disclosure, to practice this invention. For example, the RNAqueous™-Blood Module from Ambion, Inc., product number 1913, makes it possible to isolate RT-PCR-ready RNA from 0.3-0.4 ml of normal or leukemic blood in 30 minutes. RT-PCR kits are also available from Ambion, Inc. and others.

EXAMPLE 8

Identification of the hGR 1Ap/e Element(s) Activated by the Hormone

Figure 9:
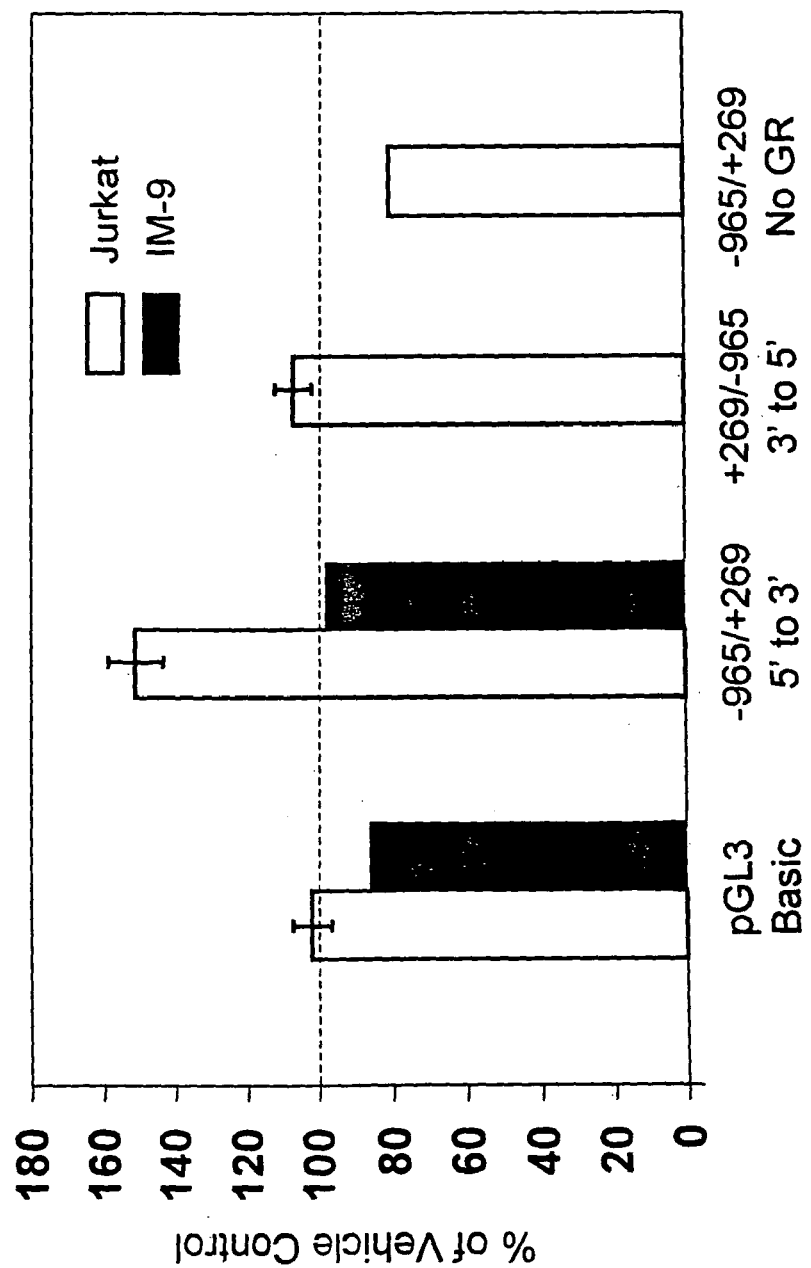
FIG. 9 illustrates the effects of glucocorticoid treatment on cells transfected with a portion of human GR 1Ap/e-luciferase constructs.

To test whether hGR 1A promoter activity is directly responsive to glucocorticoid-mediated-up-regulation, Jurkat and IM-9 cells were transiently transfected with a portion of the human GR 1Ap/e-luciferase constructs, using the procedure described in Breslin and Vedeckis, 1998. Because the Jurkat cells lack functional GR, they were cotransfected with a GR expression plasmid driven by the cytomegalovirus (CMV) constitutive promoter. All transfections included the pCH110 β-galactosidase plasmid (Pharmacia Biotech, Piscataway, N.J.), and the resulting β-galactosidase activity in each extract was used to normalize the luciferase activity for transfection efficiency as described in Breslin and Vedeckis, 1998. The cells containing the constructs were treated for 24 hr with or without 1 µM dexamethasone (Dex). The expression of the luciferase gene was assayed by incubating the extracts with luciferin substrate and measuring luminescence as described in Breslin and Vedeckis, 1998. The results are shown in FIG. 9. When the empty luciferase expression vector (pGL3 Basic, Promega Corp.), which lacked hGR 1A promoter and exon sequences, was transfected into Jurkat or IM-9 cells and then treated with Dex, no increase in luciferase activity was obtained. When a portion of the hGR 1Ap/e sequence (−965/+269) was cloned upstream of the luciferase reporter gene, Dex treatment caused an increase in luciferase activity in Jurkat cells, but not in IM-9 cells. These results indicated that the −965/+269 hGR 1Ap/e sequence has promoter activity and that its activation is specific for a T-cell (Jurkat) cell line, but is not observed in a B-cell (IM-9) cell line. Thus, the glucocorticoid-induced up-regulation of GR promoter activity appears to be cell type-specific. When a portion of the hGR 1Ap/e sequence was cloned in the opposite orientation (3' to 5') to that found normally in the gene, no increase in luciferase activity was seen in Jurkat cells treated with hormone (FIG. 9). This result indicated that the DNA sequence must be present in its normal 5' to 3' orientation, and suggests that the sequence is a bona fide promoter, because promoter activity is dependent upon the orientation of the sequence in the gene. FIG. 9 also shows that the Dex-induced luciferase activity requires the presence of functional GR within the T-cell. Even when a portion of the hGR 1Ap/e sequence (−965/+269) was in the correct 5' to 3' direction, no hormone-induced up-regulation of luciferase expression occurred when the hGR cDNA expression plasmid was not cotransfected with it into the Jurkat cells (FIG. 9).

EXAMPLE 9

Intraexonic hGR 1A Sites Controlling Basal and Hormone-Induced Promoter Activity By mapping the hGR 1Ap/e sequence, we have begun to identify the sites that control both basal and hormone-induced expression. We used DNase I footprinting as described in Breslin and Vedeckis, 1998, to identify areas of the extracted DNA that bind to proteins from a cell extract. Six footprints were identified. These footprints are shown as boxes over the sequences in SEQ ID NO: 1, and labeled Footprint 1 (FP1) through Footprint 6 (FP6) (FIG. 1). FP1 through FP4 were found in the region upstream of the transcription start site and in the putative promoter. Surprisingly, FP5 and FP6 were found in regions of the gene that are transcribed into an untranslated mRNA exon in all three exon 1A transcripts. (Data not shown).

Figure 10:
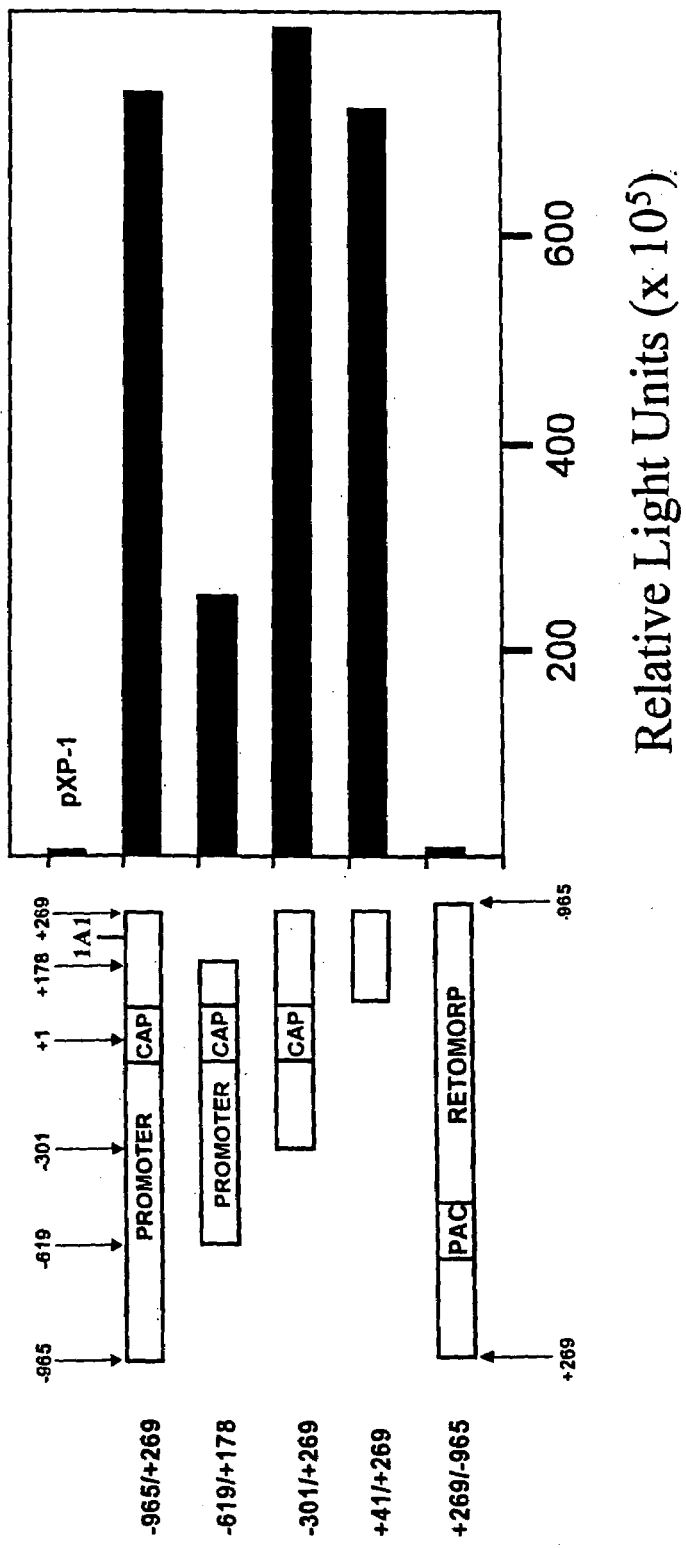
FIG. 10 illustrates the basal activity of a portion of the hGR 1Ap/e in cells transfected with various lengths of sequences of the hGR 1A promoter and exon sequences.

To determine the regions of the hGR 1Ap/e sequence (SEQ ID NO: 1) that contribute to basal (i.e., non-hormone-stimulated) expression of the exon 1A-containing transcripts, various portions of the sequence were deleted and cloned in front of a luciferase reporter gene. Transient transfection experiments (including cotransfection with the GR cDNA and the β-galactosidase normalization vector) were performed in Jurkat cells, as described in Example 8. The results are shown in FIG. 10. The "empty" luciferase vector used was pXP-1, with a very low basal promoter activity. See Breslin and Vedeckis, 1998. Placing the −965/+269 hGR 1Ap/e sequence in front of the luciferase gene increased expression about 700-fold. Deletion of this fragment at the 5' and 3' ends to give a −619/+178 fragment lowered basal promoter activity significantly. Thus, the sequence between −965 and −619, or that between +178 and +269, or both affect basal promoter activity. The deletion mutants −301/+269 and +41/+269 showed activity similar to that of the −965/+269 fragment, suggesting that the sequences between −965 and +41 are dispensable and that the sequences between +41 and +269 are most important for affecting basal promoter activity. Indeed, when the +41/+269 fragment was used alone, the basal promoter activity was about the same as that for the entire −965/+269 fragment. This result was surprising, as the +41/+269 sequence is transcribed into exon 1A. Regions that control the basal activity of promoters usually lie inside the promoter itself, that is, 5' to the start site of RNA transcription. The +41/+269 sequence is within the DNA sequence that codes for the RNA primary transcript. There may be a cryptic promoter in pXP-1 that can be activated by the +41/+269 region to allow initiation of RNA synthesis. Thus, it is expected that the +41/+269 region would increase transcription from the normal hGR 1A promoter in vivo. An alternative explanation is that an aberrant initiation of RNA synthesis can occur in the +41/+269 region in portions of the hGR1A/luciferase construct. Finally, inverting the entire −965/+269 fragment to the opposite orientation abolished promoter activity, consistent with the fact that promoters are orientation dependent.

Figure 11:
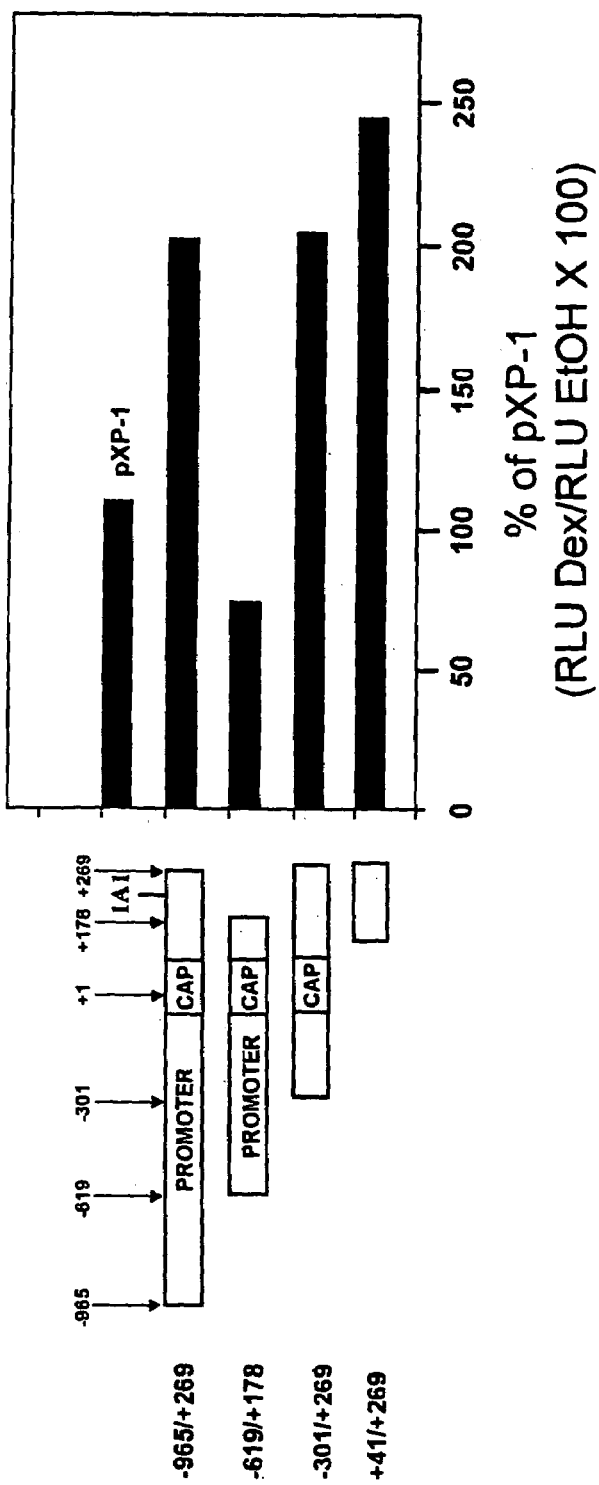
FIG. 11 illustrates the hormone inducibility of a portion of the hGR 1Ap/e in cells transfected with various lengths of sequences of the hGR 1A promoter and exon sequences.

This same series of constructs was also tested for hormone-inducibility. The results, shown in FIG. 11, are similar to those of FIG. 10. The +41/+269 fragment conferred about the same level of hormone-responsiveness as was seen with the entire −965/+269 hGR 1Ap/e sequence. The construct that lacked the +178 to +269 sequence (−691/+178 construct) showed no hormone induction.

These studies indicate that both the basal promoter activity and the hormone-inducibility of portions of the hGR 1Ap/e sequence are contained in the +41/+269 DNA sequence. This is a surprising result because these sequences are intraexonic, i.e., they are transcribed into the mRNA found in the untranslated 1A exons. Additionally, the +41/+269 fragment includes the same sequences that were unexpectedly found to give DNA footprints, FP5 (+102/+125) and FP6 (+167/+189) (see SEQ ID NO: 1).

Figure 12:
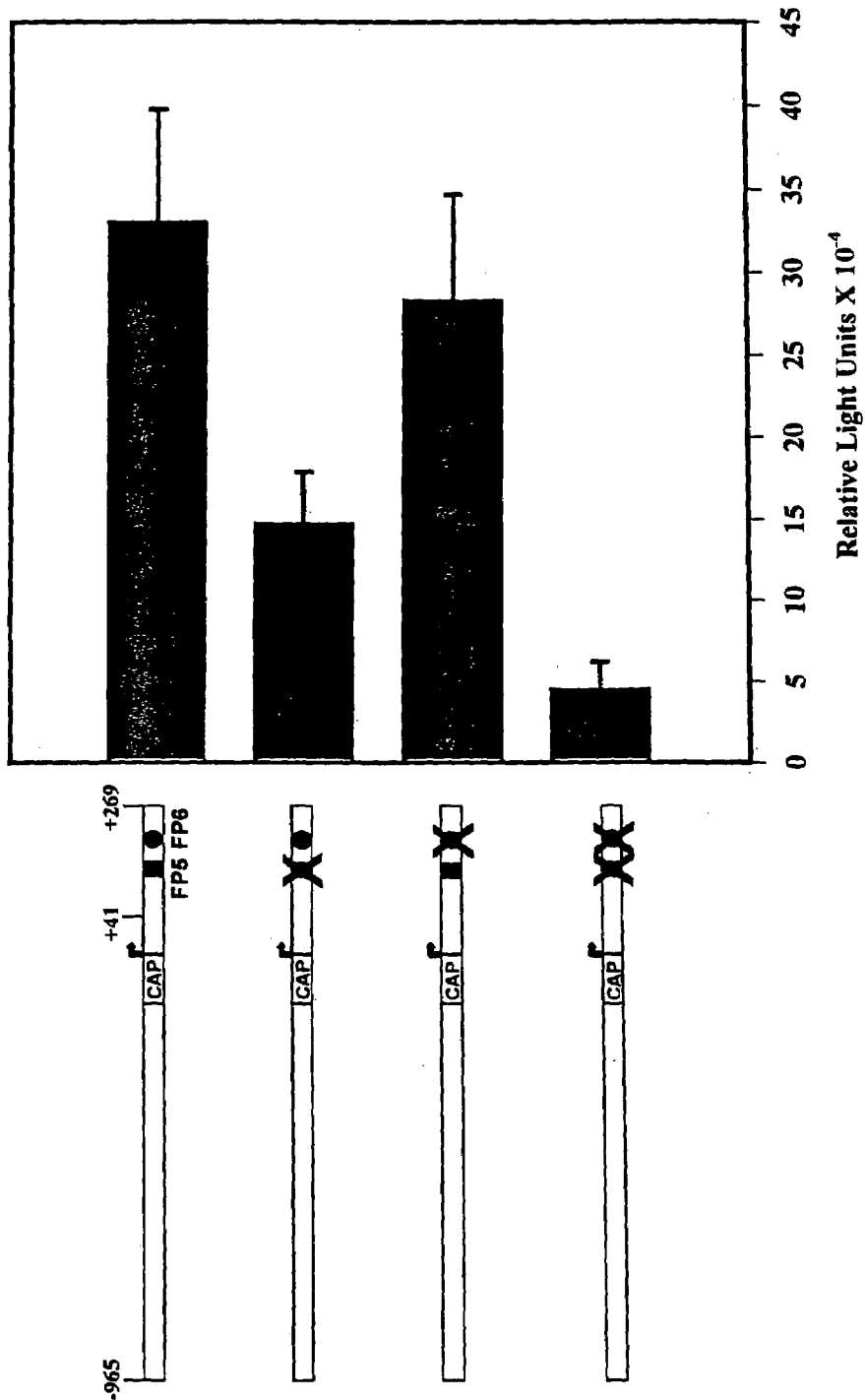
FIG. 12 illustrates the basal activity of a portion of the hGR 1Ap/e in cells transfected with constructs containing deletions in FP5 and/or FP6 in the hGR1A exon sequence.

To determine if FP5 or FP6 controlled basal promoter activity, FP5 and FP6 were deleted singly or in combination from the −965/+269 GR1Ap/e-luciferase reporter gene using the MutaGene in vitro Mutagenesis Kit (Bio-Rad laboratories, Hercules, Calif.), according to the manufacturer's instructions. The oligonucleotides used for the FP5 and FP6 deletions were FP5 deletion oligo (SEQ ID NO: 25) and FP6 deletion oligo (SEQ ID NO: 26). These constructs were transfected into the Jurkat T-cell leukemia line. The results are shown in FIG. 12. Deletion of FP5 caused a substantial decrease in basal GR promoter activity, indicating that this sequence is needed for normal basal GR gene transcription. Deletion of FP6 alone had no significant effect, indicating that it is dispensable for basal GR gene expression. However, the lowest level of basal promoter activity was observed when both DNA sequences were deleted. These results indicate that FP5 is an indispensable element for GR promoter basal activity, but that it may cooperate with FP6 to provide maximal basal promoter activity.

EXAMPLE 10

Identification of FP5 and FP6

Computer analysis using WWW Signal Scan (http://bimas.dcrt.nih.gov/molbio/signal) indicated that a portion of FP5 was similar to a DNA sequence (an Interferon Regulatory Factor Element, IRF-E) that binds the transcription factors Interferon Regulatory Factor 1 and 2 (IRF-1 and IRF-2). See N. Tanaka et al., "Recognition DNA Sequences of Interferon Regulatory Factor 1 (IRF-1) and IRF-2, Regulators of Cell Growth and the Interferon System," *Mol. Cell. Biol.*, vol. 13, pp. 4531-4538 (1993). The same analysis indicated that a portion of FP6 was similar to a DNA sequence that was homologous to a portion of a known sequence for a Glucocorticoid Response Element (GRE). See J. M. Strawhecker et al., "Binding of the 97 kDa Glucocorticoid Receptor to the 5'-Upstream Flanking Region of the Mouse c-Ha-ras Oncogene," *Oncogene*, vol. 4, pp. 1317-1322 (1989). To test if FP5 was an IRF-E and if FP6 was a GRE, electrophoretic mobility shift assays (EMSA) and antibody supershift assays were performed as described in Breslin and Vedeckis, 1998. The oligonucleotide used for the FP5 sequence was FP5(+) oligo (SEQ ID NO: 27), 5' GTAGAGGCGAATCACTTTCACTTCT-GCTGGG 3', and its complementary strand, FP5(−) oligo (SEQ ID NO: 28), 5' CCCAGCAGAAGTGAAAGTGAT-TCGCCTCTAC 3'. The underlined sequences are those that are homologous to the consensus IRF-E. See Tanaka et al. (1993). The oligonucleotide used for the FP6 sequence was FP6(+) oligo (SEQ ID NO: 29), 5' GAGAAG-GAGAAAACTTAGATCTTCTGATACCAA 3', and its complementary strand, FP6(−) oligo (SEQ ID NO: 30), 5' TTGGTATCAGAAGATCTAAGTTTTCTCCTTCTC 3'. The underlined sequences are those that are homologous to one-half of a consensus GRE. See X. Lang et al., "The Nuclear Hormone Receptor Superfamily: Structure and Function," pp. 91-126 in W. V. Vedeckis (ed.), Hormones and Cancer (1996).

Nuclear extracts from CEM-C7 cells were capable of shifting both the FP5 and FP6 oligonucleotide pairs, indicating that there were proteins in the nuclear extracts that can bind to portions of these DNA sequences. (Data not shown). See Breslin and Vedeckis (1998). Antibodies to IRF-1 and IRF-2 (Santa Cruz Biotechnology, Inc. Santa Cruz, Calif.) were added to reactions containing the FP5 sequences. A decrease in the mobility of the radioactive DNA band would indicate that the antibody was reacting with its protein antigen, which itself is bound to the labeled DNA. This would identify the protein that interacts with the specific DNA sequence. The IRF-1 antibody did not supershift the protein DNA complex. However, no supershift was obtained when a consensus IRF-E oligonucleotide was used either. Thus, it was possible that the nuclear extract did not contain functional IRF-1 or that the anti-IRF-1 antibody was incapable of supershifting the complex under the conditions tested. However, there was a supershift of the nuclear extract/FP-5 complex, and of the nuclear extract/consensus IRF-E complex, using an IRF-2 antibody. (Data not shown). This demonstrated that FP5 in the hGR 1Ap/e sequence is an interferon regulatory factor element (IRF-E).

A similar experiment was performed with FP6 and a consensus GRE. (Data not shown). The nuclear extract contained protein that was capable of binding to the FP6 sequence and the GRE, giving a band of the same mobility using EMSA. There are no antibodies available that can supershift GR/GRE complexes. Therefore, a competition experiment using an excess of FP6 oligonucleotide or unlabeled, consensus GRE oligonucleotide was performed, similar to experiments described in Breslin and Vedeckis (1998). A 2000× excess of unlabeled FP6 oligonucleotide competed for binding of nuclear protein to a labeled GRE oligonucleotide, and a 2000× excess of unlabeled GRE was able to compete for binding of protein to a labeled FP6 oligonucleotide. This indicated that there is a GRE in the FP6 sequence.

These experiments confirmed that FP5, which is a major contributor to basal hGR 1Ap/e activity, contains an IRF-E that can bind IRF-2 (and perhaps IRF-1). It seems likely that interferons, by stimulating IRF activity and levels, may be important for basal hGR 1Ap/e activity. Furthermore, FP6 contains a GRE, and is located in a region of the DNA in the hGR 1Ap/e that is stimulated by Dex (+41/+269; FIG. 11). Thus, it appears that the intraexonic region of the hGR 1Ap/e contains both an IRF-E that binds interferon regulatory factors and controls basal transcription, and a GRE that controls glucocorticoid up-regulation of hGR 1A transcripts in T-lymphoblast cells.

EXAMPLE 11

Studies of hGR 1A Promoter Regulation

Experiments will be conducted to test the hypothesis that glucocorticoid resistance in T-cell leukemia can arise from promoter silencing. There is evidence that promoter silencing occurs in breast cancer through increased methylation of the estrogen receptor and progesterone receptor promoters, leading to hormone-resistant cancers. See Y. L. Ottaviano et al., "Methylation of the Estrogen Receptor CpG Island Marks Loss of Estrogen Receptor Expression in Human Breast Cancer Cells," *Cancer Res.*, vol. 54, pp. 2552-2555 (1994) and R. G. Lapidus et al., "Methylation of Estrogen and Progesterone Receptor 5' CpG Islands Correlates with Lack of Estrogen and Progesterone Receptor Gene Expression in Breast Tumors," *Clin. Cancer Res.*, vol. 2, pp. 805-810 (1996).

To study the hGR 1A promoter, CEM-C7 cells will be cultured to obtain glucocorticoid-resistant clones derived from a single hormone-resistant cell. Individual cell clones will be obtained by limiting dilution, where 1 cell is diluted per 500 µl of medium, distributed in 50 µl aliquots in 96-well microtiter plates, making it highly probable that each well originally contains at most a single progenitor cell. See H. D. Bradshaw, Jr. and W. V. Vedeckis, "Glucocorticoid Effects on Thymidine Incorporation into the DNA of S49 Lymphoma Cells," *J. Steroid Biochem.*, vol. 18, pp. 691-698 (1983). Each resistant cell line will eventually be cultured in 40 ml of medium in a T-75 flask. Then northern blot and RT-PCR analysis will be performed for hGR 1A exon transcripts using the same exon 1A-specific probes and techniques described in Example 5 above. The exon 1A transcript level will be compared with that from wild-type (i.e., hormone-responsive) CEM-C7 cells. If the resistant variant clone contains similar basal levels of the exon 1A transcript as wild-type cells, that would suggest a mutation in the GR coding sequence that renders the GR non-functional. However, if the level of exon 1A transcript is reduced, that would suggest some type of promoter silencing mechanism. The latter could be caused, for example, by a global suppression of hGR 1A promoter usage (e.g., by methylation or by loss of a transcription factor in the cell). It could also be due to mutations in the 1A promoter sequence that lower its ability to respond to the appropriate transcription factor. By sequencing the promoter, we will determine if mutation(s) are responsible for the loss of exon 1A transcript expression.

These studies will provide answers to several questions. First, the number of hormone-resistant cell lines that have normal hGR 1A exon transcript levels will suggest the frequency with which cells become resistant due to mutations in the GR coding sequence. The number of hormone-resistant cells that show no or reduced hGR 1A exon expression will suggest the frequency with which cells become hormone resistant due to promoter mutations or promoter silencing. These frequencies could then be used to predict the frequencies with which patients become glucocorticoid resistant by each mechanism. Second, sequencing mutated promoters or coding regions will provide information about which mutations destroy functionality, and indicate possible "mutational hot spots" where the hGR 1A promoter or the GR coding region is particularly susceptible. These analyses will provide useful information for understanding how the GR 1A promoter functions. Finally, these studies will provide a diagnostic tool for screening hormone-resistant patients to identify precisely the mechanism causing hormone resistance in each patient, and to help indicate which of various alternative therapies may be best suited for each patient. For example, if the levels of GR exon 1A-containing mRNA are normal, then attempts to increase these levels further would not be useful. But if the levels were low, it will be valuable to increase these levels so that the cells become susceptible to glucocorticoid-induced apoptosis (see Example 13).

EXAMPLE 12

Test of Buffy Coats to Determine Hormone Responsiveness

We will isolate buffy coats from patients (See J. Stevens et al., "Characterization of Cytosolic and Nuclear Glucocorticoid-Binding Components in Human Leukemic Lymphocytes," *Cancer Res.*, vol. 39, pp. 4939-4948 (1979)), and treat them with a suitable dose schedule of glucocorticoid hormone (e.g., 1 µM Dex for 24 hr). Following hormone challenge, transcription of hGR 1A exon will be analyzed to evaluate hormone responsiveness using RT-PCR as described in Example 5. Buffy coats from glucocorticoid-responsive patients should respond to the hormone challenge by increasing the level of expression of hGR 1A exon, while the levels of GR 1B and GR 1C exons are not expected to change. Buffy coats from glucocorticoid-resistant patients are expected to show no change in hGR 1A exon expression in response to hormone challenge. This technique should provide an effective in vitro method of determining the hormone responsiveness of a patient. Corticosteroid could then be eliminated from the treatment of patients identified as hormone-resistant. This diagnosis will allow for dose escalation and/or the use of new chemotherapeutic drug combinations that are currently contraindicated by concomitant glucocorticoid treatment.

The RT-PCR primers and probes that will be used initially for these studies and the studies described in the previous and following examples are indicated on SEQ ID NO: 1 in FIG. 1, by underlining with dashed lines. The homology between the published mouse 1A sequence (Chen et al., 1996b) and the human hGR 1Ap/e sequence is probably not strong enough for the mouse sequences to be used for RT-PCR or RNase protection assays. Therefore, identification of the human sequence is preferred to define RT-PCR primers to detect the presence of exon 1A3.

EXAMPLE 13

Direct Activation of the 1A Promoter

The sequence of the 1A promoter and exon and identification of the transcription factors that bind to it will lead to new treatments. By identifying transcription factor binding sites in the 1A promoter and exon, we will determine whether activation of any of these factors will directly activate the hGR 1A promoter. For example, if the interferon regulatory factor element (IRF-E) that we have discovered is functional in activating the hGR 1A promoter, it may be possible to combine interferon therapy with corticosteroids to improve the lymphoblast kill rate by super-inducing GR expression. Jurkat cells have been separately treated with interferon-α, (INF-α), interferon-β (INF-β), and interferon-γ (INF-γ), and all three cause a dramatic increase in IRF-1, but not IRF-2, protein levels (data not shown). IRF-1 has been shown to stimulate gene transcription when it is bound to IRF-E, while IRF-2 inhibits gene transcription and probably blocks the stimulatory effects of the IRF-1. See H. Harada et al., "Structurally Similar but Functionally Distinct Factors, IRF-1 and IRF-2, Bind to the Same Regulatory Elements of IFN and IFN-Inducible Genes," *Cell*, vol. 58, pp. 729-739 (1989). Thus, treatment of CEM-C7 cells (or of human patients) with an interferon may increase intracellular IRF-1, which could then stimulate the transcription of exon 1A G transcripts in the lymphoblast cells. This would make these cells more sensitive to the killing effects of glucocorticoids, thus resulting in an improved therapy and patient response.

Other cytokines, lymphokines, chemokines, and hormones that activate transcription factors that bind to the 1A promoter and exon sequences may be clinically useful, for example, the proteins that bind to FP1-FP4. Another 4.4 kbp of DNA upstream of the 2056 bp of hGR 1Ap/e sequence have been subcloned, and there may be additional transcription factor binding sites in this DNA that can be activated by naturally occurring biological response modifiers.

It may also be possible to use this approach to directly activate the 1A promoter in patients who are hormone-resistant (either at presentation or at relapse), thereby driving GR levels high enough in the lymphoblasts to make them sensitive to glucocorticoid-mediated apoptosis. It has been shown that a threshold level of hGR must be present in T-lymphoblasts for glucocorticoid-mediated apoptosis to occur, and it was suggested that hormone-induced up-regulation is normally necessary for this response. See J. Ramdas et al., "Glucocorticoid-Induced Cell Death Requires Autoinduction of Glucocorticoid Receptor Expression in Human Leukemic T Cells," *Cancer Res.*, vol. 59, pp. 1378-1385 (1999). Thus, the use of biological response modifiers such as cytokines, chemokines, lymphokines, and hormones to increase GR expression in T-lymphoblast cells is expected to be useful in treating T-ALL in humans. Furthermore, the use of naturally occurring substances, instead of the non-specific cytotoxic, combination chemotherapy used currently, will have fewer side effects and produce decreased morbidity and mortality in patients.

Finally, the sequential or combined use of interferons and glucocorticoids is a new treatment for human patients. Interferons are released as an immunological response to infections, such as viral infection. Interferons stimulate the immune system response. Conversely, glucocorticoids are immunosuppressive and anti-inflammatory. Thus, the combined treatment with these two drugs is counterintuitive, as it would seem that this combination would counteract the effects of either treatment alone. However, this treatment may be of great benefit in the treatment of T-ALL. If a combination of interferon and glucocorticoid caused a synergistic up-regulation of GR in T-lymphoblast cells, a much better cell kill would be afforded by this therapy. Further, the counteracting effects of these two drugs on the immune system in general may greatly reduce side effects of the therapy, since the patient would neither have a hyperstimulated immune response (interferon alone), nor be immune-suppressed (glucocorticoid alone). That is, the systemic side effects of this combination would be reduced or abrogated, while the anti-neoplastic effect of the combined therapy would be specifically magnified.

EXAMPLE 14

Reactivation of Silenced GR Gene Expression

There is evidence that T-ALL blasts can contain normal GR coding sequences, but that expression of the GR gene is too low for the cells to be responsive to the hormone. See S. Geley et al., "Resistance to Glucocorticoid-Induced Apoptosis in Human T-Cell Acute Lymphoblastic Leukemia CEM-C1 cells is Due to Insufficient Glucocorticoid Receptor Expression. *Cancer Res.*, vol. 56, pp. 5033-5038 (1996); and Ramdas et al., 1999. In breast cancer, it has been shown that methylation of the estrogen receptor promoter and progesterone receptor promoter causes a decrease in receptor gene and protein expression, leading to a hormone-resistant state. See Ottaviano et al., 1994; and Lapidus et al., 1996. Experiments to reactivate GR gene expression by demethylating the promoter will be conducted by treating a patient with low levels of agents that inhibit DNA methylation. Two such demethylation agents are 5-azacytidine and 5-deoxyadenosine. This treatment is expected to convert leukemia cells from the hormone-resistant to the responsive phenotype, as occurs with the estrogen receptor in human breast cancer cells. See A. T. Ferguson, A. T. et al., "Demethylation of the Estrogen Receptor Gene in Estrogen Receptor-Negative Breast Cancer Cells Can Reactivate Estrogen Receptor Gene Expression, *Cancer Res.*, vol. 55, pp. 2279-2283 (1995). Similarly, treatment of hormone-resistant clones of human CEM-C7, T-ALL cells, or mouse SAK8 T-lymphoma cells in culture with the demethylating agent 5-azacytidine can cause these cells to become stably sensitive to glucocorticoid-mediated killing. See E. B. Thompson et al., "Glucocorticoid Receptors in Human Leukemias and Related Diseases," *Klin. Wochenschr.*, vol. 63, pp. 689-698 (1985); and J. C. Gasson and S. Bourgeois, "A New Determinant of Glucocorticoid Sensitivity in Lymphoid Cell Lines," *J. Cell. Biol.*, vol. 96, pp. 409-415 (1983). Methods for reactivating silenced hGR 1A promoter activity and resultant GR gene expression by various demethylating agents would allow the successful use of glucocorticoids in a larger population of relapsed leukemia patients. That is, demethylation of the hGR 1Ap/e region of the DNA in T-lymphoblast cells by treating patients with demethylating agents could allow reactivation of a silent hGR 1A promoter or convert the promoter into a state that would allow up-regulation by the hormone. This may be a way of converting hormone-resistant T-ALL patients to the hormone-responsive state and could allow the use of glucocorticoid therapy in patients who would not normally respond to this therapy.

EXAMPLE 15

Use of hGR 1Ap/e in Gene Therapy

Human gene therapy vectors will be engineered to contain all or portions of the hGR 1Ap/e sequence linked to GR cDNA in a DNA construct designed to promote overexpression of GR. See M. A. Roskrow and B. Gansbacher, "Recent Developments in Gene Therapy for Oncology and Hematology," *Crit. Rev. Oncol. Hematol.*, vol. 28, pp. 139-151 (1998). Delivery of this DNA construct into T-ALL blasts that are hormone-resistant would convert the cells to the hormone-sensitive state. Since these T-cells are then programmed to die, these genetically altered, GR-overexpressing cells will only be transiently present and not present a danger of introducing GR overexpression into other T-cells. Furthermore, studies on the IM-9 B-cell line (FIG. 8) have indicated that this construct would be down-regulated in cells other than T-cells, thus preventing the inappropriate overexpression of GR in other cell types. This type of gene replacement therapy would be useful in converting a hormone resistant T-ALL patient into a glucocorticoid sensitive type, since the patient's T-cells (after the introduction of the hGR 1Ap/e cDNA construct) will overexpress GR upon hormone treatment and be killed by the hormone.

EXAMPLE 16

Use of the hGR 1Ap/e Sequence to Regulate Heterologous Gene Expression in Gene Therapy of T-ALL All or portions of the hGR 1Ap/e sequence will be tested for the ability to act as a hormone-induced promoter to conditionally express downstream heterologous genes in various cell types, in much the same way that the mouse mammary tumor virus [MMTV] promoter has been used.

See G. Sparmann et al., "Conditional Expression of Human TNF-alpha: a System for Inducible Cytotoxicity," *Int. J. Cancer*, vol. 59, pp. 103-107 (1994); and Y. Murayama et al., "Cell-Specific Expression of the Diphtheria Toxin A-Chain Coding Sequence Under the Control of the Upstream Region of the Human Alpha-Fetoprotein Gene," *J. Surg. Oncol.*, vol. 70, 145-149 (1999). All or portions of the hGR 1Ap/e sequence will be cloned into a suitable vector, along with a heterologous toxin gene to be regulated by the hGR 1Ap/e promoter, and then be used to transform a target cell or organism. See Murayama et. al., 1999; M. W. Robertson, III, et al., "Use of a Tissue-Specific Promoter for Targeted Expression of the Herpes Simplex Thymidine Kinase Gene in Cervical Carcinoma Cells," *Cancer Gene Ther*., vol. 5, pp. 331-336 (1998); and W. H. Günzburg et al., "Regulated Gene Expression After Retroviral Vector-Mediated Delivery of Cancer-Relevant Therapeutic Genes," *Recent Results Cancer Res*., vol. 144, pp. 116-126 (1998). Since up-regulation of the human GR 1A promoter is T-cell specific, glucocorticoid treatment after this type of gene therapy would result in increased expression of the toxin gene only in T-cells. This would cause a specific killing of the T-ALL cells, leading to a novel form of therapy for this disease. It is expected that the expression of the toxin gene will be either unaffected or will actually be down-regulated in non-T-cells, as occurs for the normal hGR 1A-containing RNA transcripts in B-cells (FIG. 8). Thus, side effects and the inappropriate killing of non-T-cells should be minimal. Eventually, normal T-cells that may also be killed by this therapy would be replenished by hematopoietic stem cells as occurs, for example, after standard chemotherapy.

In the specification and the claims, a "toxin" is defined as a gene product(s) that causes or leads to the destruction or incapacitation of a cell. This definition is intended to include the induction of endogenous events leading to cell death, such as apoptosis or necrosis.

EXAMPLE 17

Cancer Screening

In addition to the applications to T-cell ALL discussed above, studies of hGR 1Ap/e expression will be conducted to determine whether it can be used as a diagnostic tool to detect other glucocorticoid-sensitive cancers, including pre-B cell leukemia and multiple myeloma. For example, glucocorticoids are also of some use in the treatment of multiple myeloma, by inhibiting the growth of the cancer cells. See M. Gomi et al., "Glucocorticoid Effects on Myeloma Cells in Culture: Correlation of Growth Inhibition with Induction of Glucocorticoid Receptor Messenger RNA," *Cancer Res*., vol. 50, pp. 1873-1878, (1990). Other cancers will be tested for glucocorticoid-stimulated up-regulation of hGR 1Ap/e expression as shown in Example 5, to identify new corticosteroid-responsive cancers. Any cancer that shows up-regulation of GR 1A-containing transcripts would be a candidate for hormone-therapy.

EXAMPLE 18

Use of 1A Promoter to Prevent Apoptosis

Excess glucocorticoid secretion has been associated with apoptosis of neurons, particularly in the part of the hippocampus that controls cognitive functions. One way to prevent apoptosis in neurons would be to express an antisense transgene to the hGR exon 1A transcripts. Thus, all or portions of the hGR 1Ap/e sequence could be linked to a fragment of the untranslated exon 1A in the antisense orientation. This construct could then be introduced into brain cells. See R. A. Kroll and E. A. Neuwelt, "Outwitting the Blood-Brain Barrier for Therapeutic Purposes: Osmotic Opening and Other Means," *Neurosurgery*, vol. 42, pp. 1083-1099 (1998). All or portions of the hGR 1A p/e could then be activated using glucocorticoids to up-regulate the antisense GR RNA. This would lower the responsiveness of the neurons to glucocorticoids and prevent hormone-induced expression of genes that cause apoptosis. Because the GR 1B and 1C transcripts are constitutively expressed and not regulated by hormone (FIG. 8), there should be enough residual GR in the cells to prevent deleterious side effects that could occur from apparent glucocorticoid deficiency. Preventing apoptosis in targeted cells such as neurons could inhibit the neuronal loss that may be involved in senility and Alzheimer's disease.

The complete disclosures of all references cited in this specification are hereby incorporated by reference. In the event of an otherwise irreconcilable conflict, however, the present specification shall control.

We claim:

1. An isolated hGR 1Ap/e polynucleotide fragment of the human glucocorticoid receptor promoter 1A and exon 1A comprising at least 2056 bases of SEQ ID NO: 1.

2. A hGR 1Ap/e polynucleotide fragment as in claim 1, wherein the receptor promoter 1A comprises the region from 1 to 1075 bases as numbered in SEQ ID NO: 1.

3. A hGR 1Ap/e polynucleotide fragment as in claim 1, wherein the exon 1A comprises the region from 1076 to 2056 bases as numbered in SEQ ID NO: 1.

4. An isolated human glucocorticoid receptor exon 1A region as in claim 3, wherein transcription of the exon region results in a mRNA transcript.

5. An isolated mRNA transcript of human glucocorticoid receptor exon 1A region as in claim 4, wherein the transcript results from transcription of the region from 1076 to 2056 bases as numbered in SEQ ID NO: 1.

* * * * *

SEQUENCE LISTING

```
<160> NUMBER OF SEQ ID NOS: 30

<210> SEQ ID NO 1
<211> LENGTH: 2056
<212> TYPE: DNA
<213> ORGANISM: Homo sapiens

<400> SEQUENCE: 1
attagagatt gtaaattggg ctctgagctt cctaccaaca aaagcacaaa ggaaaatatg      60
atcactggta ttaaaaaaaa acacctatgg tttccaaaag attaaaacaa accagcagtt     120
ttatagaagc taacactaaa atctaaagga actacgttct atggagccac ttaatatgga     180
taaacacttt gacaatattc tttcaacaac tacagtaaca agtttcttag agtccatttc     240
tttttacatc cataatgaat tgtaaatctt ttctacttct taagtaaaac atcaccactt     300
aattctggta acttttccat attaactttt tagaacaatt gcaaacgtac cataaatgat     360
```

```
tgttgtcaca gtggtaacta tttgaccctg actgttattt tgtatatagc agcttttaaa      420
ataaaaaggc aacaagtttc taggcgtaat ttccacagat ctttatgta aacaatgac        480 atcctttgca acttctgcca tttaatctat ctcaagcaag ctctctggaa acaaatctat      540
ttgaaagatt ctattgtaat tagaaatcag ggtaactgaa tgcactagat gaaaaccttc      600 tgactgggc caatgaagtc aataaagtca aaactgctgt gaatgctcaa ctgtctgcag       660
atcagatgtc ttgggatgga atccgttctc gaggccacca tcattaatat caatttggcc     720
atgtaataca agcctcactt gttccactgt tacaaatgtg cttaaaactg agctcattta     780
caatccaaat acatatgtag gatggtaacc aaggcatcac actaatttag gtattatgtt    840 ttaggggaa caaaggtat gttaatattt tattcatctc caaattaact ataaattgtg       900
cattcttgca tagatcctcc ttgggaatga gaaattagga aaatccagtt gttaaaatga    960
atgcctaaaa tcaaaataaa atttgttttt ctggcacctg cttgatgaca cagactaata   1020
accaatgaca aaattccctt gaacccaagt tttcatttcc tcctattgtg tggtcaggtt    1080
atgtaagggt ttgctttcac cccattcaaa aggtacctct tcctcttctc ttgctccctc    1140
tcgccctcat tcttgtgcct atgcagacat ttgagtagag gcgaatcact ttcacttctg   1200
ctggggaaat tgcaacacgc ttctttaaat ggcagagaga aggagaaaac ttagatcttc    1260
tgataccaaa tcactggacc ttagaaggtc agaaatcttt caagccctgc aggaccgtaa   1320
aatgcgcatg tgtccaacgg aagcactggg gcatgagtgg ggaaggaata gaaacagaaa  1380
gagggtaaga aagaaaaaa gggaaagtgg tgaaggcagg gaggaaaatt gcttagtgtg    1440
aatatgcacg cattcattta gttttcaaat ccttgttgag catgataaaa ttcccagcat    1500
cagacctcac atgttggttt ccattaggat ctgcctgggg gaatatctgc tgaatcagtg   1560
gctctgagct gaactaggaa attcaccata attaggagag tcactgtatt tctctccaaa   1620 aaaaaaaag ttatacccga gagacaggat cttctgatct gaaattttct tcacttctga   1680
aattctctgg tttgtgctca tcgttggtag ctatttgttc atcaagagtt gtgtagctgg  1740
cttcttctga aaaaggaat ctgcgtcata tctaagtcag atttcattct ggtgctctca    1800
gagcagttag cccaggaaag gggccagctt ctgtgacgac tgctgcagag gcaggtgcag  1860
tttgtgtgcc acagatatta actttgataa gcacttaatg agtgccttct ctgtgcgaga  1920
atggggagga acaaaatgca gctcctaccc tcctcgggct ttagttgtac cttaataaca   1980
ggaattttca tctgcctggc tcctttcctc aaagaacaaa gaagactttg cttcattaaa   2040
gtgtctgaga aggaag                                                    2056

<210> SEQ ID NO 2
<211> LENGTH: 1075
<212> TYPE: DNA
<213> ORGANISM: Homo sapiens

<400> SEQUENCE: 2
attagagatt gtaaattggg ctctgagctt cctaccaaca aaagcacaaa ggaaaatatg      60
atcactggta ttaaaaaaaa acacctatgg tttccaaaag attaaaacaa accagcagtt     120
ttatagaagc taacactaaa atctaaagga actacgttct atggagccac ttaatatgga    180
taaacacttt gacaatattc tttcaacaac tacagtaaca agtttcttag agtccatttc    240 ttttacatc cataatgaat tgtaaatctt ttctacttct taagtaaaac atcaccactt     300
aattctggta acttttccat attaactttt tagaacaatt gcaaacgtac cataaatgat    360
```

```
tgttgtcaca gtggtaacta tttgaccctg actgttattt tgtatatagc agcttttaaa      420
ataaaaaggc aacaagtttc taggcgtaat ttccacagat cttttatgta aaacaatgac      480
atcctttgca acttctgcca tttaatctat ctcaagcaag ctctctggaa acaaatctat      540
ttgaaagatt ctattgtaat tagaaatcag ggtaactgaa tgcactagat gaaaaccttc      600 tgactgggc caatgaagtc aataaagtca aaactgctgt gaatgctcaa ctgtctgcag       660
atcagatgtc ttgggatgga atccgttctc gaggccacca tcattaatat caatttggcc      720
atgtaataca agcctcactt gttccactgt tacaaatgtg cttaaaactg agctcattta      780
caatccaaat acatatgtag gatggtaacc aaggcatcac actaatttag gtattatgtt      840 ttaggggaa caaaaggtat gttaatattt tattcatctc caaattaact ataaattgtg       900
cattcttgca tagatcctcc ttgggaatga gaaattagga aaatccagtt gttaaaatga      960
atgcctaaaa tcaaaataaa atttgttttt ctggcacctg cttgatgaca cagactaata     1020
accaatgaca aaattccctt gaacccaagt tttcatttcc tcctattgtg tggtc          1075
```

<210> SEQ ID NO 3
<211> LENGTH: 1075
<212> TYPE: DNA
<213> ORGANISM: Mus musculus

<400> SEQUENCE: 3

```
cactggagag aatctgttaa ctggcctctc atctttctat ccagcaagca cagaaaaaca      60
aaaatgacta ctgctaaaag tctactttct agaaaccaac acggaacatt ttaggatgtt      120
aacattaaag tctaaaaaag ttctgttcag cagagcctca tgatatgggc aaggactttg      180
ccaataatct gtcagcaaac atagcatctg ctttcttaaa gtcacactct tctgttcttc      240
ctaacttgca agtaatctcc atttctcaag caacaatccc cacttgatcc tgataacctt      300
ttatttcata gtaaactctt gaaaacagtt gcacatgtac cagaaaatga tgcttgacac      360
catggaaatg atttgacaca gcagttactt tgtctccacc agttacacct ttctatagag      420
ttcccataga ggctttatgt aaagcactgg ggtgttttttg tttgtttgtt tgttttaaca     480
gctctaccat ttaatcagcc tagagaatga tctagaaacc agtctatctg aaggattcta      540
ctgagtttag aatttagtat aacaggagag agtgggtgag acccttctga tgggccctga      600
agccaagagc attggctcag ctctgagtgc caagccaag agcattggct cagctctgag       660
tgcccaagcc attgcacact gctgtgttgg catggcgttt ctgcaggcca ttggtactct      720
tactgttttg gccatgtaat tcatcgctca ctattcaact gtgacaggtg tgcttaaaac      780
gacatacctg ttcacagcct atatggtgac caggaccctg aactaacttg gaccttatgt      840
cagaagcaac aaaagacata ccaatatttt cttgattttc aaattggtaa gttaaattgt      900
ctacccttgc gtagattctc ttcaggcaaa tgaggaagtg ccagttaaag gtagtgtgta      960
aaatcaaaac aaaaattaaa ctggcacctg cgtgatgaac aaaaattata atcaatggta     1020
caactgtctg aagtcatttt catttccttc catgaagtgg gcagagttgt ggggc          1075
```

<210> SEQ ID NO 4
<211> LENGTH: 981
<212> TYPE: DNA
<213> ORGANISM: Homo sapiens

<400> SEQUENCE: 4

```
aggttatgta agggtttgct ttcaccccat tcaaaaggta cctcttcctc ttctcttgct       60
ccctctcgcc ctcattcttg tgcctatgca gacatttgag tagaggcgaa tcactttcac      120
```

-continued

| | |
|---|---|
| ttctgctggg gaaattgcaa cacgcttctt taaatggcag agagaaggag aaaacttaga | 180 |
| tcttctgata ccaaatcact ggaccttaga aggtcagaaa tctttcaagc cctgcaggac | 240 |
| cgtaaaatgc gcatgtgtcc aacggaagca ctgggcatg agtggggaag gaatagaaac | 300 |
| agaaagaggg taagagaaga aaaaagggaa agtggtgaag gcagggagga aaattgctta | 360 |
| gtgtgaatat gcacgcattc atttagtttt caaatccttg ttgagcatga taaaattccc | 420 |
| agcatcagac ctcacatgtt ggtttccatt aggatctgcc tgggggaata tctgctgaat | 480 |
| cagtggctct gagctgaact aggaaattca ccataattag gagagtcact gtatttctct | 540 |
| ccaaaaaaaa aaaagttata cccgagagac aggatcttct gatctgaaat tttcttcact | 600 |
| tctgaaattc tctggtttgt gctcatcgtt ggtagctatt tgttcatcaa gagttgtgta | 660 |
| gctggcttct tctgaaaaaa ggaatctgcg tcatatctaa gtcagatttc attctggtgc | 720 |
| tctcagagca gttagcccag gaaaggggcc agcttctgtg acgactgctg cagaggcagg | 780 |
| tgcagtttgt gtgccacaga tattaacttt gataagcact taatgagtgc cttctctgtg | 840 |
| cgagaatggg gaggaacaaa atgcagctcc taccctcctc gggctttagt tgtaccttaa | 900 |
| taacaggaat tttcatctgc ctggctcctt tcctcaaaga acaaagaaga ctttgcttca | 960 |
| ttaaagtgtc tgagaaggaa g | 981 |

<210> SEQ ID NO 5
<211> LENGTH: 981
<212> TYPE: DNA
<213> ORGANISM: Mus musculus

<400> SEQUENCE: 5

| | |
|---|---|
| taactctctt ctctcctccc tttccctctc ggtcctcccc ccccaaccc ccatgtctct | 60 |
| ctctctctct ctctctctct ctctctctct ctctctctct ctctgttttg gttccttctt | 120 |
| gctcttttta gggcctgcac agacccacgg gtagccactg atcactctca cttctgctga | 180 |
| ggaaatgaca gcatgcttct ctaaatggtg gaacgaaaga gaaacagat gttctgatac | 240 |
| caaatggtca gactttggag ggttagcagt attctcagga ccagtaggac ctagaatatc | 300 |
| tgagtctgaa gagcactggg gagtcactgg ggggtgggtc agaagactaa gacaagaaaa | 360 |
| agggaggtgg gcggatgtct gtgtgttatc tgctctgctg atccctctcg tgcatgatgc | 420 |
| aacacctgac tttaaccctc ttgctatggt ttctatttgg gtctgacttg gggactatct | 480 |
| gctgaatcag tatctctgag cagaaccaag aaattcaccc ccaaagagga gtcactgtat | 540 |
| tagtcagggt ctctgaacaa agttagaccc aagaaacaga atcctctggt ctgaaatggt | 600 |
| ctcttgtgtg aaattctctg ctttgtacgc aaaggaaaga acatgccggt aggagcctgc | 660 |
| tcgtcaaacg aggtgtgaat ctagcttctt ctagaaaaag cagcctgcgt cacatcgaag | 720 |
| ccagatttgg ttctttgctc tgagagcggt taggctagtg gagggcaggc ttccgtgaca | 780 |
| actggtacag ggacaggtgc agtgtgggtc ccacagatat gaactctgat aaatcgtgca | 840 |
| tgagctactc tgcgtaagaa tggagaagag agcagcccag ctcccaccct cctgggggttc | 900 |
| ccatcgcagc ctgatcatct gcagccttct cagccaggaa gatgtttcag atcctgcttc | 960 |
| gttagagtgt ctgggaggaa g | 981 |

<210> SEQ ID NO 6
<211> LENGTH: 27
<212> TYPE: DNA
<213> ORGANISM: Artificial Sequence
<220> FEATURE:

```
<223> OTHER INFORMATION: Description of Artificial Sequence: 5'AP-1
      primer

<400> SEQUENCE: 6
ccatcctaat acgactcact atagggc                                          27

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: exon 2,
      primer #1

<400> SEQUENCE: 7
gggttttata gaagtccatc acatctcc                                         28

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:  exon 2,
      primer #2

<400> SEQUENCE: 8
cgacagccag tgagggtgaa gacg                                             24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: G3PDH
      primer

<400> SEQUENCE: 9
gaccacagtc catgacatca ct                                               22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: -2101 to
      -1783 upstream primer

<400> SEQUENCE: 10
tccgacactg taccctacca ag                                               22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: -2101 to
      -1783 downstream primer

<400> SEQUENCE: 11
tccgacgatg ccgggaccga gcc                                              23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: antisense
```

-continued

+955/+978 primer

<400> SEQUENCE: 12
ccttctcaga cactttaatg aagc                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: exon 1A3
      primer

<400> SEQUENCE: 13
gcttcattaa agtgtctgag aagg                                          24

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:  exon 1A1
      primer

<400> SEQUENCE: 14
gtgaatatca acttctaagg tccagtg                                       27

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: exon 1A2
      primer

<400> SEQUENCE: 15
gtgaatatca actctttctg tttc                                          24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: exon 1B
      primer

<400> SEQUENCE: 16
gcaacttctc tcccagtggc g                                             21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: exon 1C
      primer

<400> SEQUENCE: 17
cttaaatagg gctctccccc                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: exon 1A
      (-372/-353) primer

```
<400> SEQUENCE: 18
ggtaaccaag gcatcacact                                              20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: exon 1A
      (-174/-149) primer

<400> SEQUENCE: 19
gatgacacag actaataacc aatg                                         24

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: exon 1a
      (+56/+77) primer

<400> SEQUENCE: 20
ttgctccctc tcgccctcat tc                                           22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: exon 1a
      (+126/+146) primer

<400> SEQUENCE: 21
ctggggaaat tgcaacacgc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: exon 1a
      (+222/+241) primer

<400> SEQUENCE: 22
ctttcaagcc ctgcaggacc                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: exon 1a
      (+456/+475) primer

<400> SEQUENCE: 23
ctgcctgggg gaatatctgc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: exon 1a
      (+84/+103, antisense) primer
```

```
<400> SEQUENCE: 24
ctactcaaat gtctgcatag                                              20

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: FP5
      deletion oligo nucleotide

<400> SEQUENCE: 25
gcaatttccc cagcagtgat tcgcctctac tc                                32

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence:  FP6
      deletion oligo nucleotide

<400> SEQUENCE: 26
cagtgatttg gtatctctaa gttttctcct tctc                              34

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: FP5 (+)
      oligo nucleotide

<400> SEQUENCE: 27
gtagaggcga atcactttca cttctgctgg g                                 31

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: FP5 (-)
      oligo nucleotide

<400> SEQUENCE: 28
cccagcagaa gtgaaagtga ttcgcctcta c                                 31

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: FP6 (+)
      oligo nucleotide

<400> SEQUENCE: 29
gagaaggaga aaacttagat cttctgatac caa                               33

<210> SEQ ID NO 30
<211> LENGTH: 33
<212> TYPE: DNA
<213> ORGANISM: Artificial Sequence
```

```
<220> FEATURE:
<223> OTHER INFORMATION: Description of Artificial Sequence: FP6 (-)
      oligo nucleotide

<400> SEQUENCE: 30
ttggtatcag aagatctaag ttttctcctt ctc                                    33
```